US008855783B2

(12) United States Patent
Dagan et al.

(10) Patent No.: US 8,855,783 B2
(45) Date of Patent: Oct. 7, 2014

(54) DETECTOR-BASED ARTERIAL STIMULATION

(75) Inventors: Amir Dagan, Kibbutz Megiddo (IL); Yossi Gross, Moshav Mazor (IL); Yotam Reisner, Kiryat Tivon (IL); Offer Glasberg, Zichron Ya'akov (IL); Nitai Hanani, Haifa (IL); Gal Ariav, Givaat Ada (IL); Oded Meiri, Moshav Ram-On (IL)

(73) Assignee: Enopace Biomedical Ltd., Caesarea Industrial Park (IL)

( * ) Notice: Subject to any disclaimer, the term of this patent is extended or adjusted under 35 U.S.C. 154(b) by 258 days.

(21) Appl. No.: 13/294,062

(22) Filed: Nov. 10, 2011

(65) Prior Publication Data
US 2013/0123880 A1  May 16, 2013

Related U.S. Application Data

(60) Provisional application No. 61/532,660, filed on Sep. 9, 2011.

(51) Int. Cl.
*A61N 1/378* (2006.01)
*A61N 1/36* (2006.01)
*A61N 1/372* (2006.01)
*A61N 1/05* (2006.01)
*A61F 2/01* (2006.01)

(52) U.S. Cl.
CPC ........... *A61N 1/372* (2013.01); *A61F 2002/016* (2013.01); *A61N 1/3615* (2013.01); *A61N 1/37217* (2013.01); *A61N 1/378* (2013.01); *A61N 1/0556* (2013.01); *A61N 1/36053* (2013.01)

USPC ................. 607/62; 600/529; 600/382; 607/6; 607/7; 607/115

(58) Field of Classification Search
CPC .................................. A61B 5/02; A61N 1/05
USPC ..................... 600/382, 529; 607/6, 7, 62, 115
See application file for complete search history.

(56) References Cited

U.S. PATENT DOCUMENTS 3,650,277 A  3/1972  Sjostrand et al.
3,661,148 A  5/1972  Kolin
(Continued)

FOREIGN PATENT DOCUMENTS

EP  0 109 935  5/1984
EP  0791341  8/1997
(Continued)

OTHER PUBLICATIONS

Sherman AJ, "Blockade of nitric oxide synthesis reduces myocardial oxygen consumption in vivo", Circulation 95:1328-1334, 1997.
(Continued)

*Primary Examiner* — Christopher D Koharski
*Assistant Examiner* — Natasha Patel
(74) *Attorney, Agent, or Firm* — Sughrue Mion, PLLC

(57) ABSTRACT

Apparatus is provided, including (1) an external device, configured for placement outside of a body of a subject and to sense a factor of the subject, and to generate a signal in response to the sensed factor, and (2) an implant, which comprises a wireless receiver for receiving the signal, and at least one electrode, the implant configured to drive the electrode to apply current to an aortic and/or vagal site of the subject in response to the signal.

31 Claims, 7 Drawing Sheets

(56) References Cited

U.S. PATENT DOCUMENTS

| | | |
|---|---|---|
| 4,154,227 A | 5/1979 | Krause et al. |
| 4,201,219 A | 5/1980 | Bozal Gonzalez |
| 4,474,630 A | 10/1984 | Planck et al. |
| 4,692,148 A | 9/1987 | Kantrowitz et al. |
| 4,791,931 A | 12/1988 | Slate |
| 4,809,681 A | 3/1989 | Kantrowitz et al. |
| 4,821,723 A | 4/1989 | Baker et al. |
| 4,938,766 A | 7/1990 | Jarvik |
| 5,192,271 A | 3/1993 | Kalb et al. |
| 5,265,011 A | 11/1993 | O'Rourke et al. |
| 5,265,601 A | 11/1993 | Mehra |
| 5,304,208 A | 4/1994 | Inguaggiato |
| 5,324,323 A | 6/1994 | Bui |
| 5,330,507 A | 7/1994 | Schwartz |
| 5,372,573 A | 12/1994 | Habib |
| 5,411,031 A | 5/1995 | Yomtov |
| 5,423,871 A | 6/1995 | Hoegnelid et al. |
| 5,454,838 A | 10/1995 | Vallana |
| 5,458,626 A | 10/1995 | Krause |
| 5,487,760 A | 1/1996 | Villafana |
| 5,533,520 A | 7/1996 | Inguaggiato |
| 5,540,733 A | 7/1996 | Testerman |
| 5,549,655 A | 8/1996 | Erickson |
| 5,591,216 A | 1/1997 | Testerman et al. |
| 5,612,314 A | 3/1997 | Stamler |
| 5,645,570 A | 7/1997 | Corbucci |
| 5,645,839 A | 7/1997 | Chobanian et al. |
| 5,649,966 A | 7/1997 | Noren et al. |
| 5,669,924 A | 9/1997 | Shaknovich |
| 5,707,400 A | 1/1998 | Terry, Jr. et al. |
| 5,762,599 A | 6/1998 | Sohn |
| 5,782,774 A | 7/1998 | Shmulewitz |
| 5,800,464 A | 9/1998 | Kieval et al. |
| 5,800,502 A | 9/1998 | Boutos |
| 5,900,433 A | 5/1999 | Igo et al. |
| 5,902,712 A | 5/1999 | Axelgaard |
| 5,904,712 A | 5/1999 | Axelgaard |
| 5,906,641 A | 5/1999 | Thompson et al. |
| 5,913,876 A | 6/1999 | Taylor |
| 5,925,061 A | 7/1999 | Ogi et al. |
| 5,935,077 A | 8/1999 | Ogle |
| 5,944,680 A | 8/1999 | Christopherson et al. |
| 5,948,006 A | 9/1999 | Mann |
| 5,967,986 A | 10/1999 | Cimochowski et al. |
| 5,994,444 A | 11/1999 | Trescony et al. |
| 6,023,640 A | 2/2000 | Ross |
| 6,038,485 A | 3/2000 | Axelgaard |
| 6,053,873 A | 4/2000 | Govari |
| 6,058,331 A | 5/2000 | King |
| 6,086,527 A | 7/2000 | Talpade |
| 6,106,477 A | 8/2000 | Miesel et al. |
| 6,120,520 A | 9/2000 | Saadat |
| 6,141,587 A | 10/2000 | Mower et al. |
| 6,200,259 B1 | 3/2001 | March |
| 6,212,435 B1 | 4/2001 | Lattner et al. |
| 6,240,316 B1 | 5/2001 | Richmond |
| 6,245,103 B1 | 6/2001 | Stinson |
| 6,277,078 B1 | 8/2001 | Porat et al. |
| 6,280,377 B1 | 8/2001 | Talpade |
| 6,298,268 B1 | 10/2001 | Ben-Haim |
| 6,345,202 B2 | 2/2002 | Richmond |
| 6,347,247 B1 | 2/2002 | Dev |
| 6,363,279 B1 | 3/2002 | Ben-Haim |
| 6,411,845 B1 | 6/2002 | Mower et al. |
| 6,445,953 B1 | 9/2002 | Bulkes |
| 6,463,323 B1 | 10/2002 | Conrad-Vlasak |
| 6,463,324 B1 | 10/2002 | Ben-Haim |
| 6,485,524 B2 | 11/2002 | Strecker |
| 6,522,926 B1 | 2/2003 | Kieval et al. |
| 6,575,994 B1 | 6/2003 | Marin et al. |
| 6,616,613 B1 | 9/2003 | Goodma et al. |
| 6,616,624 B1 | 9/2003 | Kieval et al. |
| 6,622,041 B2 | 9/2003 | Terry, Jr. et al. |
| 6,631,296 B1 | 10/2003 | Parramon et al. |
| 6,632,991 B2 | 10/2003 | Chen |
| 6,641,542 B2 | 11/2003 | Cho et al. |
| 6,647,287 B1 | 11/2003 | Peel, III |
| 6,721,603 B2 | 4/2004 | Zabara et al. |
| 6,770,022 B2 | 8/2004 | Mechlenburg et al. |
| 6,810,286 B2 | 10/2004 | Donovan |
| 6,824,561 B2 | 11/2004 | Soykan |
| 6,845,267 B2 | 1/2005 | Harrison |
| 6,850,801 B2 | 2/2005 | Kieval et al. |
| 6,865,416 B2 | 3/2005 | Dev et al. |
| 6,871,092 B2 | 3/2005 | Piccone |
| 6,885,895 B1 | 4/2005 | Whitehurst |
| 6,939,345 B2 | 9/2005 | KenKnight |
| 6,947,792 B2 | 9/2005 | Ben-Haim et al. |
| 6,957,107 B2 | 10/2005 | Rogers et al. |
| 6,985,774 B2 | 1/2006 | Kieval et al. |
| 7,025,730 B2 | 4/2006 | Cho et al. |
| 7,044,981 B2 | 5/2006 | Liu et al. |
| 7,062,318 B2 | 6/2006 | Ben-Haim et al. |
| 7,077,810 B2 | 7/2006 | Lange |
| 7,079,901 B1 | 7/2006 | Loftin et al. |
| 7,082,336 B2 | 7/2006 | Ransbury et al. |
| 7,090,648 B2 | 8/2006 | Sackner et al. |
| 7,158,832 B2 | 1/2007 | Kieval et al. |
| 7,167,751 B1 | 1/2007 | Whitehurst et al. |
| 7,201,719 B2 | 4/2007 | Feliss et al. |
| 7,206,637 B2 | 4/2007 | Salo |
| 7,225,019 B2 | 5/2007 | Jahns et al. |
| 7,229,403 B2 | 6/2007 | Schock |
| 7,269,457 B2 | 9/2007 | Shafer et al. |
| 7,277,749 B2 | 10/2007 | Gordon |
| 7,291,113 B2 | 11/2007 | Satoh |
| 7,292,886 B1 | 11/2007 | Kroll |
| 7,299,091 B2 | 11/2007 | Barrett et al. |
| 7,314,451 B2 | 1/2008 | Halperin |
| 7,389,149 B2 | 6/2008 | Rossing et al. |
| 7,395,119 B2 | 7/2008 | Hagen et al. |
| 7,452,334 B2 | 11/2008 | Gianchandani |
| 7,471,986 B2 | 12/2008 | Hatlestad |
| 7,476,200 B2 | 1/2009 | Tal |
| 7,486,991 B2 | 2/2009 | Libbus et al. |
| 7,623,926 B2 | 11/2009 | Rossing et al. |
| 7,660,632 B2 | 2/2010 | Kirby et al. |
| 7,680,538 B2 | 3/2010 | Durand et al. |
| 7,706,884 B2 | 4/2010 | Libbus |
| 7,706,886 B2 | 4/2010 | Morimoto et al. |
| 7,711,438 B2 | 5/2010 | Lattner |
| 7,720,547 B2 | 5/2010 | Denker et al. |
| 7,725,194 B2 | 5/2010 | Klostermann et al. |
| 7,747,302 B2 | 6/2010 | Milledge |
| 7,765,000 B2 | 7/2010 | Zhang et al. |
| 7,797,050 B2 | 9/2010 | Libbus et al. |
| 7,811,221 B2 | 10/2010 | Gross |
| 7,848,820 B2 | 12/2010 | Abrahamson |
| 7,917,226 B2 | 3/2011 | Nghiem |
| 8,065,019 B2 | 11/2011 | Marnfeldt et al. |
| 8,070,708 B2 | 12/2011 | Rottenberg |
| 8,249,705 B1 | 8/2012 | Kieval |
| 8,463,392 B2 | 6/2013 | Aghassian |
| 8,521,293 B2 | 8/2013 | Anderson et al. |
| 8,538,535 B2 | 9/2013 | Gross et al. |
| 8,571,664 B2 | 10/2013 | Anderson et al. |
| 8,600,511 B2 | 12/2013 | Yared et al. |
| 8,612,014 B2 | 12/2013 | Rahman et al. |
| 8,626,290 B2 | 1/2014 | Dagan |
| 8,626,299 B2 | 1/2014 | Gross et al. |
| 8,634,928 B1 | 1/2014 | O'Driscoll et al. |
| 8,639,339 B2 | 1/2014 | Bange et al. |
| 8,663,103 B2 | 3/2014 | Causey, III et al. |
| 8,670,835 B2 | 3/2014 | Park et al. |
| 8,692,717 B2 | 4/2014 | Friedman |
| 8,700,157 B2 | 4/2014 | Goetz et al. |
| 8,700,173 B2 | 4/2014 | Edlund |
| 2001/0044434 A1 | 11/2001 | Lee et al. |
| 2002/0016615 A1 | 2/2002 | Dev |
| 2002/0026228 A1 | 2/2002 | Schauerte |
| 2002/0032468 A1 | 3/2002 | Hill |
| 2002/0077554 A1 | 6/2002 | Schwartz |
| 2002/0089458 A1 | 7/2002 | Allen et al. |
| 2002/0103454 A1 | 8/2002 | Sackner |

(56) References Cited

U.S. PATENT DOCUMENTS

| | | |
|---|---|---|
| 2002/0169413 A1 | 11/2002 | Keren |
| 2003/0036773 A1 | 2/2003 | Whitehurst |
| 2003/0050683 A1 | 3/2003 | Boutos |
| 2003/0055465 A1 | 3/2003 | Ben-Haim et al. |
| 2003/0055466 A1 | 3/2003 | Ben-Haim et al. |
| 2003/0055467 A1 | 3/2003 | Ben-Haim et al. |
| 2003/0060858 A1 | 3/2003 | Kieval et al. |
| 2003/0130715 A1 | 7/2003 | Boutos |
| 2003/0199806 A1 | 10/2003 | Kieval |
| 2003/0204206 A1 | 10/2003 | Padua |
| 2004/0010303 A1* | 1/2004 | Bolea et al. ............ 607/118 |
| 2004/0019364 A1 | 1/2004 | Kieval et al. |
| 2004/0019368 A1 | 1/2004 | Lattner |
| 2004/0039417 A1 | 2/2004 | Soykan |
| 2004/0044393 A1 | 3/2004 | Yarden |
| 2004/0054384 A1 | 3/2004 | Nachum |
| 2004/0064090 A1 | 4/2004 | Keren |
| 2004/0106954 A1 | 6/2004 | Whitehurst et al. |
| 2004/0106976 A1 | 6/2004 | Bailey et al. |
| 2004/0111006 A1 | 6/2004 | Alferness |
| 2004/0133240 A1 | 7/2004 | Adams |
| 2004/0162590 A1 | 8/2004 | Whitehurst et al. |
| 2004/0193092 A1 | 9/2004 | Deal |
| 2004/0254616 A1 | 12/2004 | Rossing et al. |
| 2005/0027346 A1 | 2/2005 | Arkusz et al. |
| 2005/0033407 A1 | 2/2005 | Weber et al. |
| 2005/0049680 A1 | 3/2005 | Fischell et al. |
| 2005/0085868 A1 | 4/2005 | Tehrani |
| 2005/0090867 A1 | 4/2005 | Lapanashvili |
| 2005/0096710 A1 | 5/2005 | Kieval et al. |
| 2005/0143785 A1 | 6/2005 | Libbus |
| 2005/0149130 A1 | 7/2005 | Libbus |
| 2005/0149132 A1 | 7/2005 | Libbus |
| 2005/0149155 A1 | 7/2005 | Scheiner et al. |
| 2005/0154418 A1 | 7/2005 | Kieval et al. |
| 2005/0165457 A1 | 7/2005 | Benser |
| 2005/0203610 A1 | 9/2005 | Tzeng |
| 2005/0209652 A1 | 9/2005 | Whitehurst et al. |
| 2005/0232965 A1 | 10/2005 | Falotico |
| 2005/0233962 A1 | 10/2005 | Lue et al. |
| 2005/0240229 A1 | 10/2005 | Whitehurst et al. |
| 2005/0251212 A1 | 11/2005 | Kieval et al. |
| 2005/0288651 A1 | 12/2005 | Van Tassel et al. |
| 2006/0004417 A1 | 1/2006 | Rossing et al. |
| 2006/0004420 A1 | 1/2006 | Rossing et al. |
| 2006/0004430 A1 | 1/2006 | Rossing et al. |
| 2006/0074453 A1 | 4/2006 | Kieval et al. |
| 2006/0100668 A1 | 5/2006 | Ben-David |
| 2006/0111626 A1 | 5/2006 | Rossing et al. |
| 2006/0149124 A1 | 7/2006 | Forsell |
| 2006/0149345 A1 | 7/2006 | Boggs et al. |
| 2006/0167540 A1 | 7/2006 | Masters et al. |
| 2006/0173507 A1 | 8/2006 | Mrva et al. |
| 2006/0184206 A1 | 8/2006 | Baker et al. |
| 2006/0217588 A1 | 9/2006 | Gross et al. |
| 2006/0217772 A1 | 9/2006 | Libbus et al. |
| 2006/0224076 A1 | 10/2006 | Lange |
| 2006/0229677 A1 | 10/2006 | Moffit et al. |
| 2006/0259085 A1 | 11/2006 | Zhang et al. |
| 2006/0265038 A1 | 11/2006 | Hagen et al. |
| 2006/0276844 A1 | 12/2006 | Alon |
| 2006/0293712 A1 | 12/2006 | Kieval et al. |
| 2007/0021673 A1 | 1/2007 | Arbel et al. |
| 2007/0021786 A1 | 1/2007 | Parnis et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027496 A1 | 2/2007 | Parnis et al. |
| 2007/0038255 A1 | 2/2007 | Kieval et al. |
| 2007/0038259 A1 | 2/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0049989 A1 | 3/2007 | Rossing et al. |
| 2007/0060972 A1 | 3/2007 | Kieval et al. |
| 2007/0067000 A1 | 3/2007 | Strother et al. |
| 2007/0100433 A1 | 5/2007 | Limon |
| 2007/0106340 A1 | 5/2007 | Bolea et al. |
| 2007/0142879 A1 | 6/2007 | Greenberg et al. |
| 2007/0150009 A1 | 6/2007 | Kveen et al. |
| 2007/0156179 A1 | 7/2007 | S.E. |
| 2007/0156198 A1 | 7/2007 | Rossing et al. |
| 2007/0156201 A1 | 7/2007 | Rossing et al. |
| 2007/0167984 A1 | 7/2007 | Kieval et al. |
| 2007/0173893 A1 | 7/2007 | Pitts |
| 2007/0185540 A1 | 8/2007 | Ben-Haim et al. |
| 2007/0185542 A1 | 8/2007 | Bolea et al. |
| 2007/0185543 A1 | 8/2007 | Rossing et al. |
| 2007/0191904 A1* | 8/2007 | Libbus et al. ............ 607/44 |
| 2007/0196428 A1 | 8/2007 | Glauser et al. |
| 2007/0198064 A1 | 8/2007 | Lapanashvili et al. |
| 2007/0248676 A1 | 10/2007 | Stamler et al. |
| 2007/0248850 A1 | 10/2007 | Heller |
| 2007/0276270 A1 | 11/2007 | Tran |
| 2007/0276442 A1 | 11/2007 | Hagen et al. |
| 2007/0276459 A1 | 11/2007 | Rossing et al. |
| 2007/0282385 A1 | 12/2007 | Rossing et al. |
| 2007/0293927 A1 | 12/2007 | Frank et al. |
| 2008/0004673 A1 | 1/2008 | Rossing et al. |
| 2008/0009916 A1 | 1/2008 | Rossing et al. |
| 2008/0009917 A1 | 1/2008 | Rossing et al. |
| 2008/0021336 A1 | 1/2008 | Dobak |
| 2008/0046016 A1 | 2/2008 | Ben-David et al. |
| 2008/0046054 A1 | 2/2008 | Hjelle et al. |
| 2008/0051767 A1 | 2/2008 | Rossing et al. |
| 2008/0051849 A1 | 2/2008 | Ben-Haim et al. |
| 2008/0058872 A1 | 3/2008 | Brockway et al. |
| 2008/0058889 A1 | 3/2008 | Ben-Haim et al. |
| 2008/0058891 A1 | 3/2008 | Ben-Haim et al. |
| 2008/0071363 A1 | 3/2008 | Tuval et al. |
| 2008/0082137 A1 | 4/2008 | Kieval et al. |
| 2008/0097540 A1 | 4/2008 | Bolea et al. |
| 2008/0119898 A1 | 5/2008 | Ben-David |
| 2008/0119911 A1 | 5/2008 | Rosero |
| 2008/0132972 A1 | 6/2008 | Shuros et al. |
| 2008/0140167 A1 | 6/2008 | Hagen et al. |
| 2008/0154349 A1 | 6/2008 | Rossing et al. |
| 2008/0161865 A1 | 7/2008 | Hagen et al. |
| 2008/0161887 A1 | 7/2008 | Hagen et al. |
| 2008/0167690 A1 | 7/2008 | Cody et al. |
| 2008/0167693 A1 | 7/2008 | Kieval et al. |
| 2008/0167694 A1 | 7/2008 | Bolea et al. |
| 2008/0167696 A1 | 7/2008 | Cates et al. |
| 2008/0167699 A1 | 7/2008 | Kieval et al. |
| 2008/0171923 A1 | 7/2008 | Bolea et al. |
| 2008/0172101 A1 | 7/2008 | Bolea et al. |
| 2008/0172104 A1 | 7/2008 | Kieval et al. |
| 2008/0177364 A1 | 7/2008 | Bolea et al. |
| 2008/0195174 A1 | 8/2008 | Walker et al. |
| 2008/0215117 A1 | 9/2008 | Gross et al. |
| 2009/0005859 A1 | 1/2009 | Keilman |
| 2009/0030471 A1 | 1/2009 | Rousso |
| 2009/0036975 A1 | 2/2009 | Ward |
| 2009/0062874 A1 | 3/2009 | Teacey et al. |
| 2009/0112285 A1* | 4/2009 | Cahan et al. ............ 607/48 |
| 2009/0160716 A1 | 6/2009 | Rhodes et al. |
| 2009/0177090 A1 | 7/2009 | Grunwald |
| 2009/0198097 A1 | 8/2009 | Gross |
| 2009/0198308 A1 | 8/2009 | Gross |
| 2009/0204170 A1 | 8/2009 | Hastings |
| 2009/0228078 A1 | 9/2009 | Zhang et al. |
| 2009/0234418 A1 | 9/2009 | Kieval |
| 2010/0010556 A1 | 1/2010 | Zhao |
| 2010/0042186 A1 | 2/2010 | Ben-David et al. |
| 2010/0076247 A1 | 3/2010 | Zilbershlag |
| 2010/0094373 A1 | 4/2010 | Sharma |
| 2010/0125310 A1 | 5/2010 | Wilson |
| 2010/0211131 A1 | 8/2010 | Williams et al. |
| 2010/0305392 A1 | 12/2010 | Gross et al. |
| 2011/0093036 A1 | 4/2011 | Mashiach |

(56) References Cited

U.S. PATENT DOCUMENTS

| | | |
|---|---|---|
| 2011/0118773 A1 | 5/2011 | Gross |
| 2011/0137370 A1 | 6/2011 | Gross |
| 2011/0152965 A1 | 6/2011 | Mashiach |
| 2012/0035679 A1 | 2/2012 | Dagan |
| 2012/0035711 A1 | 2/2012 | Gross |
| 2012/0158081 A1 | 6/2012 | Gross |
| 2013/0043736 A1 | 2/2013 | Zilbershlag |
| 2013/0310629 A1 | 11/2013 | Lafontaine |
| 2013/0338748 A1 | 12/2013 | Dagan |
| 2014/0031607 A1 | 1/2014 | Zilberschlag et al. |

FOREIGN PATENT DOCUMENTS

| | | |
|---|---|---|
| WO | 99/26530 | 6/1999 |
| WO | 00/02501 | 1/2000 |
| WO | 02/26314 | 4/2002 |
| WO | 03/076008 | 9/2003 |
| WO | 03/082080 | 10/2003 |
| WO | 03/082403 | 10/2003 |
| WO | 2004/014456 | 2/2004 |
| WO | 2004/073484 | 9/2004 |
| WO | 2005/065771 A1 | 7/2005 |
| WO | 2005/074361 | 8/2005 |
| WO | 2005/084389 | 9/2005 |
| WO | 2005/097256 | 10/2005 |
| WO | 2006/012033 | 2/2006 |
| WO | 2006/012050 | 2/2006 |
| WO | 2006/032902 | 3/2006 |
| WO | 2006/041664 | 4/2006 |
| WO | 2006/064503 | 6/2006 |
| WO | 2006/094273 | 9/2006 |
| WO | 2006/098928 | 9/2006 |
| WO | 2006/123346 | 11/2006 |
| WO | 2006/125163 | 11/2006 |
| WO | 2006/137067 | 12/2006 |
| WO | 2007/013065 | 2/2007 |
| WO | 2007/047152 | 4/2007 |
| WO | 2007/064895 | 6/2007 |
| WO | 2007/106533 | 9/2007 |
| WO | 2007/113818 | 10/2007 |
| WO | 2007/113833 | 10/2007 |
| WO | 2007/114860 | 10/2007 |
| WO | 2007/118090 | 10/2007 |
| WO | 2007/136850 | 11/2007 |
| WO | 2007/136851 | 11/2007 |
| WO | 2008/039982 | 4/2008 |
| WO | 2008/083120 | 7/2008 |
| WO | 2008/083235 | 7/2008 |
| WO | 2008/100390 | 8/2008 |
| WO | 2009/017647 | 2/2009 |
| WO | 2009/095918 | 8/2009 |
| WO | 2009/095920 | 8/2009 |
| WO | 2012/017437 A1 | 2/2012 |
| WO | 2012/085907 | 6/2012 |
| WO | 2013/035092 A2 | 3/2013 |
| WO | 2013/069020 A1 | 5/2013 |
| WO | 2013/164829 A1 | 11/2013 |

OTHER PUBLICATIONS

Kugiyama K, "Nitric oxide activity is deficient in spasm arteries of patients with coronary spastic angina", Circulation 94:266-272, 1996.

Sabbah H et al., "Global left ventricular remodeling with the Acorn Cardiac Support Device: Hemodynamic and angiographic findings in dogs with heart failure", Heart Failure 10(2): 109-115, 2005. (Only First Page).

"Improving the Thromboresistivity of Chemical Sensors via Nitric Oxide Release: Fabrication and in Vivo Evaluation of NO-Releasing Oxygen-Sensing Catheters," by MH Schoenfisch et al., Anal. Chem., 72 (6), 1119-1126, 2000.

"Endogenous and Exogenous Nitric Oxide Protect Against Intracoronary Thrombosis and Reocclusion After Thrombolysis," by Yao et al., Circulation. 1995;92: 1005-1010.

"Improving the biocompatibility of in vivo sensors via nitric oxide release," by Jae Ho Shin et al., Analyst, 2006, 131, 609-615.

Cheetah Medical Inc. manufactures the Cheetah Reliant, Jan. 23, 2008.

Sulzer IntraTherapeutics Inc. manufactures the IntraCoil® Self-Expanding Peripheral Stent (IntraCoil® Stent), Jun. 28, 2002.

"Comparison of neurogenic contraction and relaxation in canine corpus cavernosum and penile artery and vein", Hayashida, et al. Jpn. J. Pharmacol. 72:231-240 (1996), p. 232 col. 2, para 1; p. 238, col. 2, para 2.

An International Search Report and a Written Opinion both dated Jul. 13, 2009, which issued during the prosescution of Applicant's PCT/IL09/000117.

An International Search Report and a Written Opinion both dated May 12, 2009, which issued during the prosecution of Applicant's PCT/IL09/000115.

An Office Action dated Nov. 18, 2009, which issued during the prosecution of Applicant's U.S. Appl. No. 12/023,900.

A press release dated Mar. 28, 2007 regarding the Endosure Wireless AAA Measurement System manufactured by CardioMEMS Inc.

"Vagus nerve stimulation as a method to temporarily slow or arrest the heart," by Matheny, Ann Thorac Surg. Jun. 1997;63(6 Suppl):S28-9—an abstract.

A press release dated Jan. 22, 2008 regarding the Cheetah Reliant manufactured by Cheetah Medical.

"Heart rate variability," by Task Force of the European Society of Cardiology and the North American Society of Pacing and Electrophysiology, European Heart Journal (1996) 17, 354-381.

"Heart rate and vasomotor control during exercise," by Vallais, Proceedings of the 29th Annual International Conference of the IEEE EMBS, Cité Internationale, Lyon, France, Aug. 23-26, 2007.

"Effects of chronic baroreceptor stimulation on the autonomic cardiovascular regulation in patients with drug-resistant arterial hypertension," by Wustmann, Hypertension 2009;54;530-536.

Biosense Webster, Inc. (CA, USA) manufactures the LASSO 2515 Variable Circular Mapping Catheter, Jul. 22, 2003.

"Sympathovagal balance is major determinant of short-term blood pressure variability in healthy subjects," by Laitinen, Am J Physiol Heart Circ Physiol 276:1245-1252, 1999.

"Optimal frequency ranges for extracting information on cardiovascular autonomic control from the blood pressure and pulse interval spectrograms in mice," by Baudrie, Am J Physiol Regul Integr Comp Physiol 292: R904-R912, 2007.

"Neural influences on cardiovascular variability: possibilities and pitfalls," by Malpas, Am J Physiol Heart Circ Physiol 282: H6-H20, 2002.

"Vagus nerve stimulation decreases left ventricular contractility in vivo in the human and pig heart," by Lewis, J Physiol. Jul. 15, 2001; 534(Pt 2): 547-552.

An International Preliminary Examination Report on Patentability dated Aug. 3, 2010, which issued during the prosecution of Applicant's PCT/IL09/000117.

An International Preliminary Examination Report on Patentability dated Aug. 3, 2010, which issued during the prosecution of Applicant's PCT/IL09/000115.

"Preparation and characterization of implantable sensors with nitric oxide release coatings," by MC Frost, Microchemical Journal vol. 74 Issue: 3, Jun. 2003 pp. 277-288—selected sections attached.

"Beneficial effects of nitric oxide on cardiac diastolic function: the flip side of the coin," by Paulus WJ, Heart Failure Review 5(4):337-344 (2000)—only first page.

"Loss of nitric oxide production in the coronary circulation after the development of dilated cardiomyopathy: a specific defect in the neural regulation of coronary blood flow," by Gong Zhao, Clinical and Experimental Pharmacology and Physiology 23(8): 715-721 (1996)—an abstract.

An International Search Report and a Written Opinion both dated Dec. 19, 2011, which issued during the prosecution of Applicant's PCT/IL11/00636.

An Office Action dated Oct. 2, 2012, which issued during the prosecution of U.S. Appl. No. 12/851,214.

An Office Action dated Sep. 18, 2012, which issued during the prosecution of U.S. Appl. No. 12/023,896.

(56) References Cited

OTHER PUBLICATIONS

An English Translation of an Office Action dated Oct. 8, 2012, which issued during the prosecution of Chinese Patent Application No. 200980111617.8.
Web page relating to EndoSure® Wireless AAA Pressure Measurement System, manufactured by CardioMEMS, Inc., Nov. 30, 2010 (downloaded from: http://www.cardiomems.com/content.asp?display=medical+mb&expand=ess.
An Office Action dated Jun. 19, 2012, which issued during the prosecution of U.S. Appl. No. 11/995,904.
An Office Action dated Jul. 18, 2012, which issued during the prosecution of U.S. Appl. No. 13/210,778.
An Office Action dated Mar. 15, 2012, which issued during the prosecution of U.S. Appl. No. 12/792,227.
An Office Action dated Aug. 29, 2012, which issued during the prosecution of U.S. Appl. No. 12/792,227.
An International Search Report and a Written Opinion both dated Jul. 5, 2012, which issued during the prosecution of Applicant's PCT/IL11/00952.
An Office Action dated Mar. 13, 2012, which issued during the prosecution of U.S. Appl. No. 12/023,896.
The unequal influences of the left and right vagi on the control of the heart and pulmonary artery in the rattlesnake, Crotalus durissus, by Taylor, The Journal of Experimental Biology 212, 145-151 Aug. 2008.
Coronary vascular sympathetic beta-receptor innervation, by Hamiton, American Journal of Physiology, vol. 230, No. 6, Jun. 1976.
An Office Action dated Aug. 9, 2011, which issued during the prosecution of U.S. Appl. No. 12/023,896.
Young et al. Wireless powering and data telemetry for biomedical implants IEE Eng. Med Biol Soc. 2009. Abstract.
de Balthasar, C (2005) Attachment of leads to RF-BION® microstimulators. 10th Annual Conference of the International FES Society.
Eisele et al Tongue neuromuscular and direct hypoglossal nerve stimulation for obstructive sleep apnea Otolaryngol Clin N Am 36 (2003) 501-510.
Harrision et al Wireless Neural Recording with Single Low-Power Integrated Circuit. IEEE Trans Neural Syst. 2009, 17 (4): 322-329.
Hu et al Percutaneous Biphasic Electrical Stimulation for Treatment of Obstructive Sleep Apnea Syndrome IEE Eng. Med Biol Soc. 2007. Abstract.
Loeb et al The BION devices injectable interfaces with peripheral, Neurosurg Focus 20 (5), E2, 2006.
Mann et al The Effect of Neuromuscular Stimulation of the Genioglossus, Laryngoscope 112, Feb. 2002, 351-356.
Oliven et al Effect of coactivation of tongue protrusor and retractor muscles on pharyngeal lumen and airflow in sleep apnea patients, J Appl Physiol 103: 1662-1668, 2007.
Oliven et al Electrical stimulation of the genioglossus to improve pharyngeal patency in OSA, Harefuah May 2009, 148(5): 315-319. Abstract.
Oliven et al Sublingual electrical stimulation of the tongue during wakefulness and sleep, Respiration Physiology 127 (2001), 217-226.
Oliven et al Upper airway response to electrical stimulation of the genioglossus i n OSA, J Appl Physiol 95: 2023-2029, 2003.
Printout of MedGadget.com—Implantable Neurostimulators Fight Snoring, Mar. 8, 2006. (1/5) Abstarct.
Schwartz et al Electrical Stimulation of the lingual musculature in OSA. The American Physiological Society 1996, 643-652.
Tran et al Development of asynchronous, intralingual electrical stimulation to treat OSA, IEE Eng. Med Biol Soc. 2003, 375-378. Abstract.
Tran et al First subject evaluated with simulated BION™ treatment in genioglossus to prevent OSA. IEE Eng. Med Biol Soc. 2004, Abstract.
An International Search Report and a Written Opinion both dated Apr. 17, 2012, which issued during the prosecution of Applicant's PCT/IL12/00870.
An Office Action dated Aug. 1, 2012, which issued during the prosecution of U.S. Appl. No. 12/957,799.
U.S. Appl. No. 61/131,284, filed Jun. 6, 2008.
U.S. Appl. No. 61/532,660, filed Sep. 9, 2011.
U.S. Appl. No. 61/557,083, filed Nov. 8, 2011.
U.S. Appl. No. 61/183,319, filed Jun. 2, 2009.
U.S. Appl. No. 61/331,453, filed May 5, 2010.
U.S. Appl. No. 61/641,388, filed May 2, 2012.
U.S. Appl. No. 61/714,277, filed Oct. 16, 2012.
An International Search Report and a Written Opinion both dated Aug. 8, 2013, which issued during the prosecution of Applicant's PCT/IL2013/050375.
A Supplementary European search Report dated Dec. 14, 2012, which issued during the prosecution of European Patent Application No. 06766171.
An Office Action dated Mar. 12, 2013, which issued during the prosecution of U.S. Appl. No. 13/210,778.
An Office Action dated Mar. 12, 2013, which issued during the prosecution of U.S. Appl. No. 12/957,799.
An Office Action dated Apr. 25, 2013, which issued during the prosecution of U.S. Appl. No. 11/995,904.
An Office Action dated May 10, 2013, which issued during the prosecution of U.S. Appl. No. 12/023,896.
An Office Action dated Apr. 5, 2013, which issued during the prosecution of U.S. Appl. No. 12/792,227.
An Office Action dated Dec. 20, 2013, which issued during the prosecution of U.S. Appl. No. 12/792,227.
Extended European Search Report dated Oct. 31, 2013 which issued during the prosecution of Applicant's European App No. 11814203.3.
An Office Action dated Nov. 12, 2013, which issued during the prosecution of U.S. Appl. No. 11/995,904.
An Office Action dated Jan. 27, 2014, which issued during the prosecution of U.S. Appl. No. 12/023,896.
Office Action issued in U.S. Appl. No. 13/249,062, dated Dec. 13, 2013.

\* cited by examiner

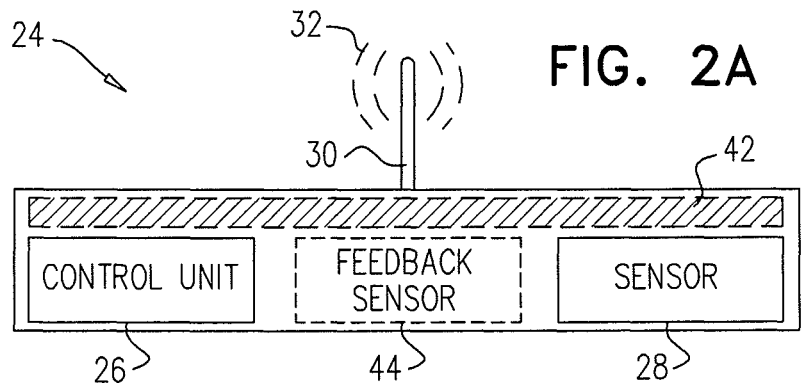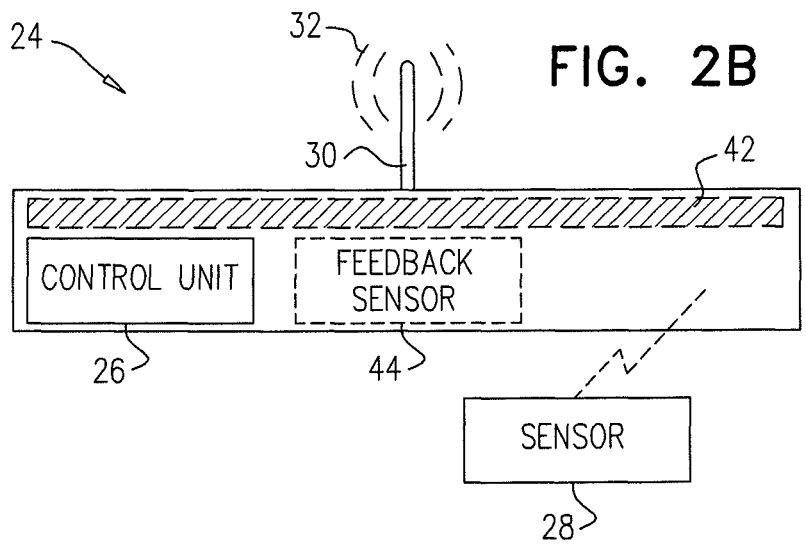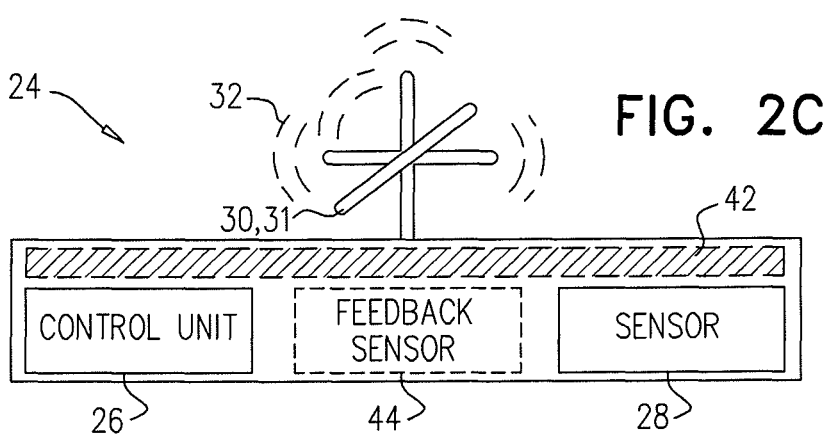

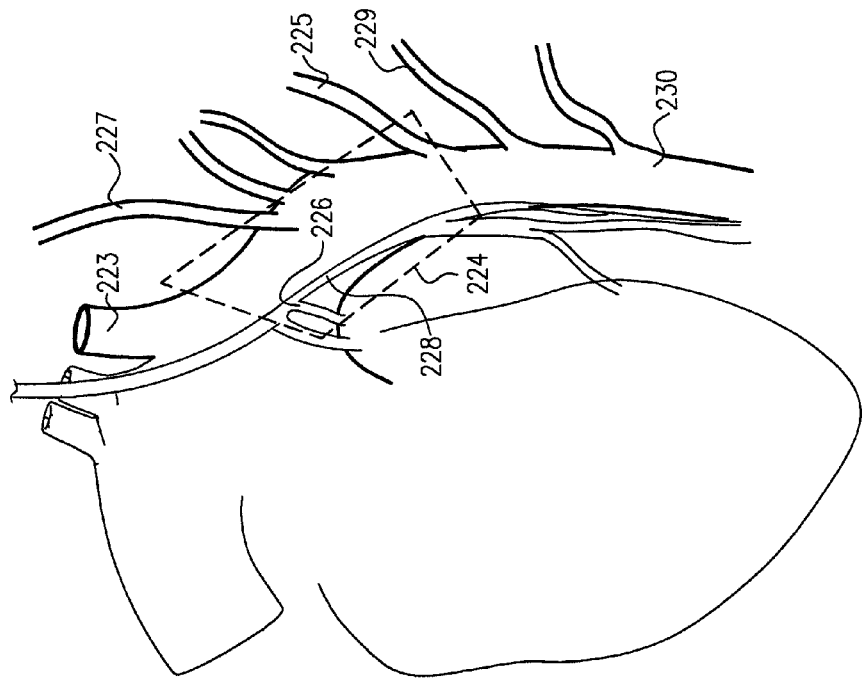
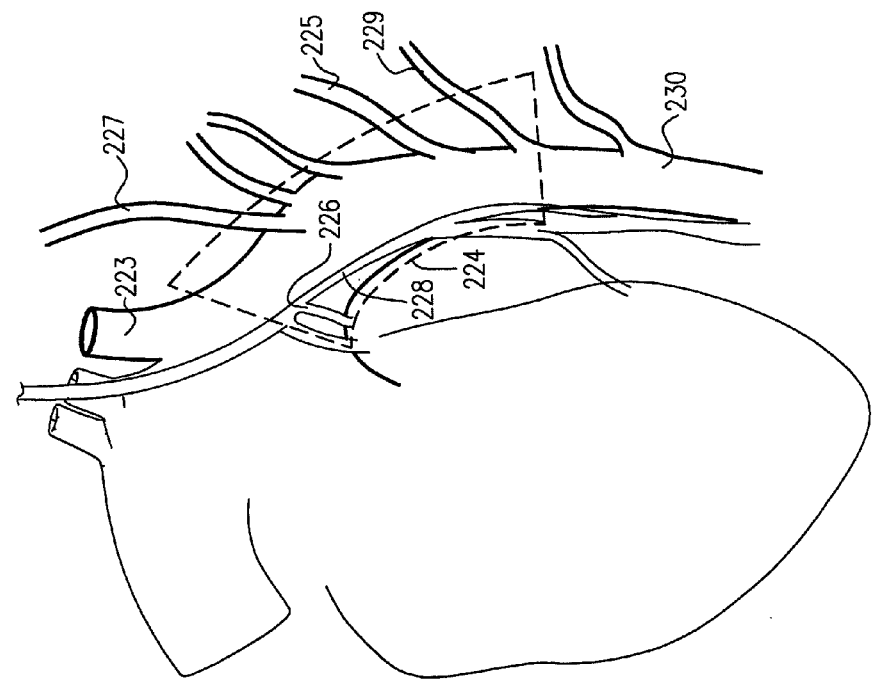

DETECTOR-BASED ARTERIAL STIMULATION

CROSS-REFERENCES TO RELATED APPLICATIONS

The present application is related to U.S. Provisional Application 61/532,660, filed Sep. 9, 2011, which is incorporated herein by reference.

FIELD OF THE INVENTION

Some applications of the present invention generally relate to medical apparatus. Specifically, some applications of the present invention relate to apparatus and methods for treating congestive heart failure, diastolic heart failure, hypertension, pulmonary hypertension, and/or other conditions.

BACKGROUND

Heart failure is a condition in which a problem with the structure or function of the heart impairs its ability to supply sufficient blood flow to meet the body's needs. The condition impairs quality of life and is a leading cause of hospitalizations and mortality in the western world. Treatment of heart failure is typically aimed at removal of precipitating causes, prevention of deterioration in cardiac function, and control of congestive state.

Hypertension, or chronic high blood pressure, is an extremely prevalent medical condition, which can lead to strokes, heart attacks, and heart failure. There are a variety of treatments that are available for treating hypertension, including lifestyle changes, and medication.

SUMMARY OF THE INVENTION

For some applications of the present invention, a subject suffering from congestive heart failure, diastolic heart failure, hypertension, and/or another disorder is identified. The subject is typically treated by implanting at least one electrode on the subject's vagus nerve at a vagal site and/or at an aortic site that is typically as described hereinbelow. Typically, a plurality of electrodes are implanted at the vagal site, and/or the aortic site. The subject is treated by driving a current into the electrode implantation site. The effects of driving the current into the implantation site typically include ventricular and aortic pressure reduction, an increase in aortic compliance, a decrease in sympathetic tone, a decrease in heart rate, and/or an increase in parasympathetic tone. These effects are typically advantageous in treating heart failure.

In some applications of the invention, an external device is used to detect one or more factors associated with the disorder of the subject. The external device transmits a signal, which is received by an implant. The implant is configured and positioned to stimulate an electrode implantation site of the subject, at least in part responsively to the received signal. Typically, the apparatus is configured to operate only when the external device is located in proximity to the subject. For example, in some applications of the invention, the external device is located in, near or under a bed and/or chair of the subject, such that detection of the factors by the external device, and/or detection of the signal by the implant, occur only when the subject is in/on the bed and/or chair.

In some applications of the invention, the implant functions by stimulating a portion of the aorta (i.e., an aortic site) of the subject that is between the bifurcation of the aorta with the left subclavian artery and the bifurcation of the aorta with the fifth intercostal artery. For example the aortic site may be (a) between the bifurcation of the aorta with the left subclavian artery and a location 4 cm downstream of the bifurcation, (b) between the bifurcation of the aorta with the left subclavian artery and the bifurcation of the aorta with the fourth intercostal artery, (c) between the bifurcation of the aorta with the left subclavian artery and the bifurcation of the aorta with the first intercostal artery, and/or (d) between the bifurcations of the aorta with the first and fifth intercostal arteries.

In some applications, the aortic site is adjacent to a portion of a vagus nerve of the subject that is between (a) a vagal bifurcation with a thoracic cardiac branch from a left recurrent laryngeal of the subject, and (b) thoracic vagal branching into the esophageal plexus of the subject. In some applications, the aortic site is adjacent to a portion of a vagus nerve of the subject that is between (a) an upper junction of a left thoracic vagal trunk with the left subclavian artery, and (b) a vagal bifurcation with a thoracic cardiac branch from a left recurrent laryngeal of the subject.

In some applications of the invention, the implant functions by stimulating a portion of the vagus nerve (i.e., a vagal site) of the subject that is between (a) a vagal bifurcation with a thoracic cardiac branch from a left recurrent laryngeal of the subject, and (b) thoracic vagal branching into the esophageal plexus of the subject. In some applications, the vagal site is between (a) an upper junction of a left thoracic vagal trunk with the left subclavian artery, and (b) a vagal bifurcation with a thoracic cardiac branch from a left recurrent laryngeal of the subject.

In some applications of the invention, the implant receives power wirelessly. In some applications, the implant receives power via electromagnetic induction. In some applications, the implant receives power via electromagnetic radiation.

There is therefore provided, in accordance with an application of the present invention, apparatus for treating a subject, the apparatus including:

an external device, configured for placement outside of the subject, the external device including:
    a detector, configured to detect a factor associated with a state of the subject; and
    a control unit, couplable to the detector, configured to automatically generate a signal at least in part responsively to the detected factor; and
an implant, including:
    a receiver, configured to receive the signal;
    an effector element, including at least one electrode, and being couplable to an aortic site of the subject; and
    a driver unit, coupled to the receiver, and configured to drive the electrode to stimulate an electrode implantation site of the subject, at least in part responsively to the signal.

In an application, the detector is configured to detect a factor associated with a disorder of the subject.

In an application, the detector is configured to detect a factor associated with a physiological state of the subject.

In an application, the electrode is configured to be placed in contact with an aortic site that is adjacent to a portion of a vagus nerve of the subject that is between (a) a vagal bifurcation with a thoracic cardiac branch from a left recurrent laryngeal of the subject, and (b) thoracic vagal branching into the esophageal plexus of the subject.

In an application, the electrode is configured to be placed in contact with an aortic site that is adjacent to a portion of a vagus nerve of the subject that is between (a) an upper junction of a left thoracic vagal trunk with the left subclavian artery, and (b) a vagal bifurcation with a thoracic cardiac branch from a left recurrent laryngeal of the subject.

In an application, the driver unit is configured to reduce ventricular pressure of the subject.

In an application, the driver unit is configured to reduce aortic pressure of the subject.

In an application, the driver unit is configured to reduce sympathetic tone of the subject.

In an application, the driver unit is configured to increase parasympathetic tone of the subject.

In an application, the driver unit is configured to increase parasympathetic tone of the subject and reduce sympathetic tone of the subject.

In an application, the detector is configured to detect a breathing-related factor of the subject.

In an application, the external device is configured to detect reclining of the subject, and to generate the signal at least in part responsively to the reclining of the subject.

In an application, the external device is configured to detect sitting of the subject, and to generate the signal at least in part responsively to the detecting of the sitting of the subject.

In an application, the implant is configured to detect reclining of the subject, and the driver unit is configured to drive the effector element at least in part responsively to the reclining of the subject.

In an application, the detector is configured to detect an electrical factor of the subject.

In an application, the detector is configured to detect chest movement of the subject.

In an application, the detector is configured to detect arterial pulses of the subject.

In an application, the detector is configured to detect a body position of the subject.

In an application, the detector is configured to detect an oxygen saturation of the subject.

In an application, the detector is configured to detect a nasal airflow of the subject.

In an application, the control unit is configured to generate the signal as a radio frequency signal.

In an application, the control unit is configured to generate the signal as a magnetic signal.

In an application, the electrode is configured to be placed in contact with an aorta of the subject.

In an application, the electrode is configured to be placed in contact with an aortic site that is between (a) the bifurcation of the aorta with a left subclavian artery and (b) the bifurcation of the aorta with a fifth intercostal artery of the subject.

In an application, the electrode is configured to be placed in contact with an aortic site that is between (a) the bifurcation of the aorta with the left subclavian artery and (b) a bifurcation of the aorta with a fourth intercostal artery of the subject.

In an application, the electrode is configured to be placed in contact with an aortic site that is between (a) the bifurcation of the aorta with the left subclavian artery and (b) a bifurcation of the aorta with a first intercostal artery of the subject.

In an application, the electrode is configured to be placed in contact with an aortic site that is between (a) the bifurcation of the aorta with the fifth intercostal artery and (b) the bifurcation of the aorta with the fourth intercostal artery of the subject.

In an application, the driver unit is configured to reduce a ratio of a low frequency component to a high frequency component of heart rate variability of the subject.

In an application, the driver unit is configured to reduce a ratio of (1) a low frequency component of less than 0.05 Hz, to (2) a high frequency component of between 0.15 and 0.35 Hz, of heart rate variability of the subject.

In an application, the implant is configured to wirelessly receive power.

In an application, the implant is configured to receive the power from the signal.

In an application, the control unit is configured to generate a second signal, and the implant is configured to receive the power from the second signal.

In an application, the implant is configured to receive power via magnetic induction.

In an application, the external device is configured to transmit power via magnetic induction.

In an application, the implant is configured to receive power via electromagnetic radiation transmitted by the external device.

In an application, the implant includes a rectifying antenna configured to receive the power.

There is further provided, in accordance with an application of the present invention, apparatus for treating a subject, the apparatus including:

an external device, configured for placement outside of the subject, the external device including:
a detector, configured to detect a factor associated with a state of the subject; and
a control unit, couplable to the detector, configured to automatically generate a signal at least in part responsively to the detected factor; and
an implant, including:
a receiver, configured to receive the signal;
an effector element, including at least one electrode, and being couplable to a vagal site of the subject; and
a driver unit, coupled to the receiver, and configured to drive the electrode to stimulate an electrode implantation site of the subject, at least in part responsively to the signal.

In an application, the detector is configured to detect a factor associated with a disorder of the subject.

In an application, the detector is configured to detect a factor associated with a physiological state of the subject.

In an application, the electrode is configured to be placed in contact with a vagus nerve of the subject.

In an application, the electrode is configured to be placed in contact with a vagal site that is between (a) a vagal bifurcation with a thoracic cardiac branch from a left recurrent laryngeal of the subject, and (b) thoracic vagal branching into the esophageal plexus of the subject.

In an application, the electrode is configured to be placed in contact with a vagal site that is between (a) an upper junction of a left thoracic vagal trunk with the left subclavian artery, and (b) a vagal bifurcation with a thoracic cardiac branch from a left recurrent laryngeal of the subject.

There is further provided, in accordance with an application of the present invention, a method for treating a subject, the method including:

extracorporeally detecting a factor associated with a state of the subject;
automatically extracorporeally generating a signal, at least in part responsively to the detected factor;
intracorporeally detecting the signal; and
automatically stimulating an aortic site of the subject, at least in part responsively to the signal.

In an application, extracorporeally detecting the factor includes extracorporeally detecting a factor associated with a disorder of the subject.

In an application, extracorporeally detecting the factor includes extracorporeally detecting a factor associated with a physiological state of the subject.

In an application, extracorporeally detecting the factor includes extracorporeally detecting the factor while the subject is sleeping.

In an application, extracorporeally detecting the factor includes extracorporeally detecting a breathing-related factor of the subject.

In an application, extracorporeally detecting the factor includes extracorporeally detecting an electrical factor of the subject.

In an application, extracorporeally detecting the factor includes extracorporeally detecting a heart cycle of the subject.

In an application, stimulating the aortic site includes stimulating an aortic site that is adjacent to a portion of a vagus nerve of the subject that is between (a) a vagal bifurcation with a thoracic cardiac branch from a left recurrent laryngeal of the subject, and (b) thoracic vagal branching into the esophageal plexus of the subject.

In an application, stimulating the aortic site includes stimulating an aortic site that is adjacent to a portion of a vagus nerve of the subject that is between (a) an upper junction of a left thoracic vagal trunk with the left subclavian artery, and (b) a vagal bifurcation with a thoracic cardiac branch from a left recurrent laryngeal of the subject.

In an application, stimulating the electrode implantation site includes reducing ventricular pressure of the subject.

In an application, stimulating the electrode implantation site includes reducing aortic pressure of the subject.

In an application, stimulating the electrode implantation site includes reducing sympathetic tone of the subject.

In an application, stimulating the electrode implantation site includes increasing parasympathetic tone of the subject.

In an application, stimulating the electrode implantation site includes increasing parasympathetic tone of the subject and reducing sympathetic tone of the subject.

In an application, stimulating the electrode implantation site includes increasing aortic compliance of the subject.

In an application, intracorporeally detecting the signal includes wirelessly receiving power via the signal, using an implant, and automatically altering the blood flow includes powering the implant using the received power.

In an application, intracorporeally detecting the signal includes wirelessly receiving data via the signal, using an implant, and automatically altering the blood flow includes operating the implant responsively to the received data.

In an application,
intracorporeally detecting the signal includes wirelessly receiving power via the signal, using an implant, and automatically altering the blood flow includes powering the implant using the received power, and
intracorporeally detecting the signal includes wirelessly receiving data via the signal, using the implant, and automatically altering the blood flow includes operating the implant responsively to the received data.

In an application, generating the signal includes generating a radio frequency signal, and detecting the signal includes detecting the radio frequency signal.

In an application, generating the signal includes generating a magnetic signal, and detecting the signal includes detecting the magnetic signal.

In an application, stimulating the aortic site includes stimulating an aortic site that is between (a) the bifurcation of the aorta with a left subclavian artery and (b) the bifurcation of the aorta with a fifth intercostal artery of the subject.

In an application, stimulating the aortic site includes stimulating an aortic site that is between (a) the bifurcation of the aorta with the left subclavian artery and (b) a bifurcation of the aorta with a fourth intercostal artery of the subject.

In an application, stimulating the aortic site includes stimulating an aortic site that is between (a) the bifurcation of the aorta with the left subclavian artery and (b) a bifurcation of the aorta with a first intercostal artery of the subject.

In an application, stimulating the aortic site includes stimulating an aortic site that is between (a) the bifurcation of the aorta with the fifth intercostal artery and (b) the bifurcation of the aorta with the fourth intercostal artery of the subject.

In an application, stimulating the electrode implantation site includes reducing a ratio of a low frequency component to a high frequency component of heart rate variability of the subject.

In an application, stimulating the electrode implantation site includes reducing a ratio of (1) a low frequency component of less than 0.05 Hz, to (2) a high frequency component of between 0.15 and 0.35 Hz, of heart rate variability of the subject.

There is further provided, in accordance with an application of the present invention, a method for treating a subject, the method including:
extracorporeally detecting a factor associated with a state of the subject;
automatically extracorporeally generating a signal, at least in part responsively to the detected factor;
intracorporeally detecting the signal; and
automatically stimulating a vagal site of the subject, at least in part responsively to the signal.

In an application, stimulating the vagal site includes stimulating a portion of a vagus nerve of the subject.

In an application, stimulating the vagal site includes stimulating a vagal site that is between (a) a vagal bifurcation with a thoracic cardiac branch from a left recurrent laryngeal of the subject, and (b) thoracic vagal branching into the esophageal plexus of the subject.

In an application, stimulating the vagal site includes stimulating a vagal site of the subject that is between (a) an upper junction of a left thoracic vagal trunk with the left subclavian artery, and (b) a vagal bifurcation with a thoracic cardiac branch from a left recurrent laryngeal of the subject.

The present invention will be more fully understood from the following detailed description of embodiments thereof, taken together with the drawings, in which:

BRIEF DESCRIPTION OF THE DRAWINGS

FIGS. 2A-C are schematic illustrations of the external device, in accordance with some applications of the present invention;

FIGS. 4A-D are schematic illustrations of electrode implantation sites, in accordance with some applications of the present invention.

DETAILED DESCRIPTION OF EMBODIMENTS

Figure 1:
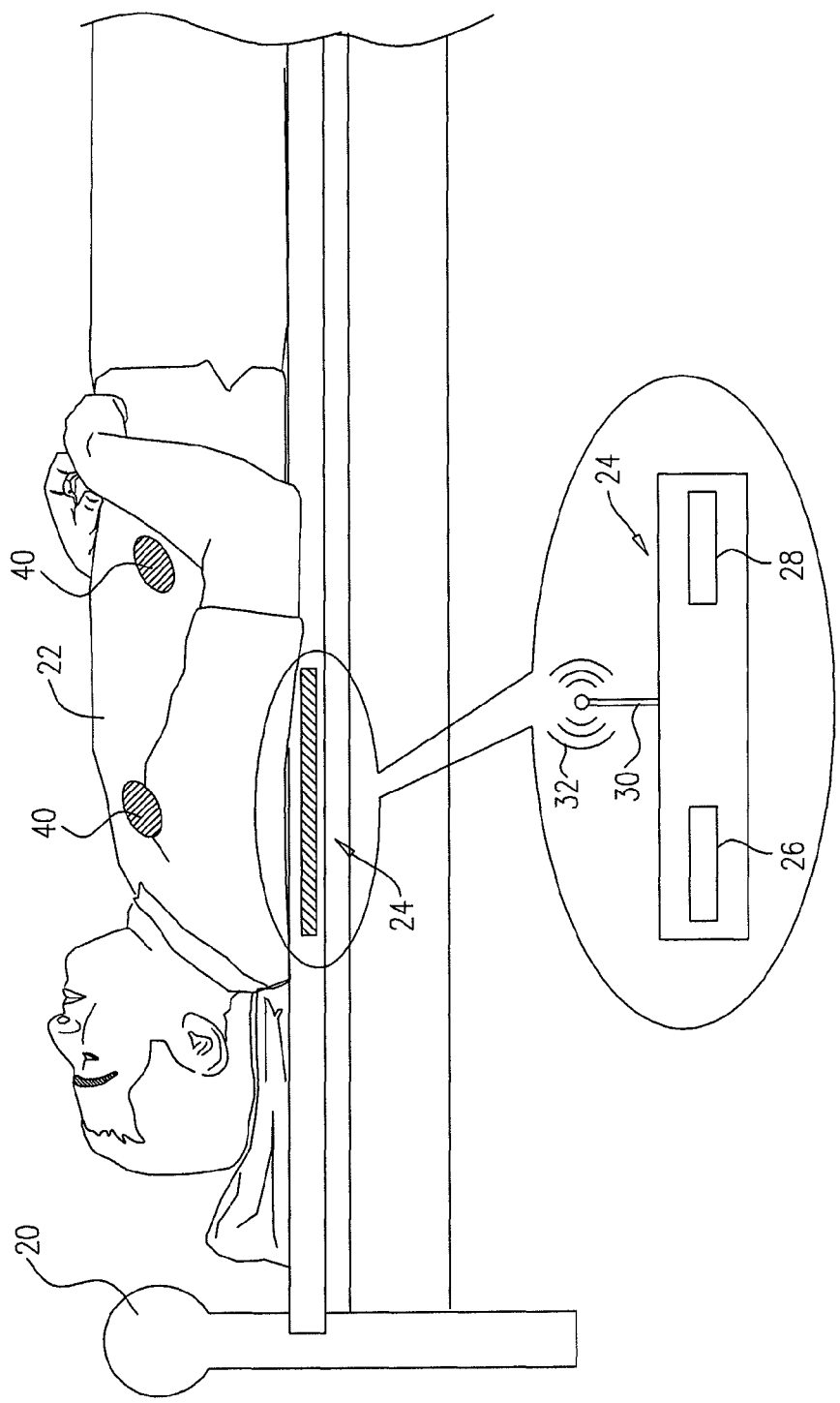
FIG. 1 is a schematic illustration of an implant implanted in a subject, and an external device in a vicinity of the subject, in accordance with some applications of the present invention.

Reference is made to FIG. 1, which is a schematic illustration of a bed 20 and a subject 22 lying in the bed. Typically, the subject is sleeping. Typically, an external device 24 comprises a control unit 26, a sensor 28, and one or more antennas 30. For some applications of the invention, external device 24 is flexible and/or contained within a soft and/or flexible container. The sensor senses one or more parameters of a state of the subject. The parameters sensed are typically indicative of a pathology of the subject. Alternatively or additionally, the parameters sensed may not be indicative of a pathology of the subject, e.g., the parameters may be physiological parameters. For example, the sensor may detect parameters of the subject that are indicative of an episode of, and/or deterioration in, congestive heart failure (CHF), diastolic heart failure, arrhythmia, tachycardia, bradycardia, dyspnea, respiratory rate disorder, and/or hypertension, and/or symptoms thereof. For example, the sensor may detect an electrical factor (e.g., an electrocardiogram), a breathing-related factor (e.g., chest movement, oxygen saturation, and/or nasal airflow), arterial pulses, and/or body position of the subject. External device 24 transmits one or more signals 32 to an implant 40, which is typically implanted in a vicinity of (e.g., at, or adjacent to) an electrode implantation site, such as a vagal site 222 and/or at an aortic site 224, as described hereinbelow. Implant 40 typically provides electrical stimulation to the subject, and is described in more detail with reference to FIGS. 3A-C. Typically, signals 32 are transmitted at least in part in response to the sensed parameters. In some applications of the invention, signals 32 are alternatively or additionally transmitted according to a set program. In some applications of the invention, signals 32 are alternatively or additionally transmitted continuously, such that implant 40 receives the signals when the implant is within a range (e.g., less than 10 m, e.g., less than 5 m, e.g., less than 1 m) of the external device.

External device 24, in accordance with some applications of the present invention, is placed in proximity to the subject, under the subject, under or inside the subject's pillow or mattress, or on another part of the bed (e.g., on a bedpost). Alternatively, the external device can be placed on, in, or under a chair of the subject. Alternatively, the external device can be placed anywhere near the subject, such that implant 40 receives signals 32 from the external device. For some applications of the invention, external device 24 is portable and/or wearable by the subject. External device 24 may be coupled to and/or disposed within an item of clothing (e.g., a hat; a belt) of the subject, or worn on a chest-band. The antennas 30 of external device 24 are typically configured to send signals 32 to the implant, as described hereinbelow.

External device 24 typically sends signals 32 to implant 40. At least in part responsively to signals 32, implant 40 provides electrical stimulation at the site of implantation. For some applications, external device 24 sends signals 32 to implant 40 for a pre-determined length of time or in a particular pattern, or both. For some applications, periods of no stimulation by implant 40 are provided. In addition, external device 24 may be configured to only provide signals 32 to implant 40 when subject 22 is reclining (e.g., when the subject is sleeping). For example, in some applications, a sensor (e.g., sensor 28) is positioned in, on or under a mattress, and configured to detect the weight of the subject, and control unit 26 is configured to only transmit signals 32 when the weight of the subject is detected. Alternatively or additionally, as described hereinbelow (e.g., with reference to FIGS. 3A-C), in some applications, implant 40 may be configured to only respond to signals 32 when the subject is reclining (e.g., when the subject is sleeping). For some applications (e.g., as described hereinbelow with reference to FIG. 3C), implant 40 detects the cardiac cycle of the subject, and provides electrical stimulation at the site of implantation at least in part responsively to the cardiac cycle (e.g., only during systole). Optionally, this stimulation is provided at least in part responsively to the cardiac cycle, but not in response to the real-time detection of any pathology or any deterioration of a pathology. For some applications, implant 40 provides stimulation to the subject at the implantation site, in accordance with protocols that are as described hereinbelow with reference to FIGS. 4A-D, and FIG. 5.

Typically, signals 32 comprise data, and implant 40 receives the data and responds to the data. In some applications of the invention, external device 24 wirelessly powers implant 40 via wireless power 132, as described hereinbelow. When external device 24 wirelessly powers implant 40, wireless power 132 may comprise signals 32 and, thereby, comprise the data to which implant 40 typically responds. For some applications of the invention, the data may comprise an on/off command. For some applications of the invention, and as described hereinbelow (e.g., with reference to FIGS. 2A and 3A-C), implant 40 may be configured to only function when wireless power 132 is being received. In these applications, signals 32 may comprise only wireless power 132. That is, when signals 32 (i.e., wireless power 132) are received by implant 40, the implant is commanded (i.e., enabled) to function, and when signals 32 (i.e., wireless power 132) are not received by the implant, the implant is commanded not to function (i.e., is disabled from operating).

One or more of the implants are typically implanted into the subject at the aortic site and/or at the vagal site of the subject. These one or more implants 40 may be configured to work in conjunction with other implants or independent of each other and/or external device 24. It is noted that the number of implants 40 in the illustration is by way of illustration and not limitation.

Closed-loop control (i.e., feedback control) is typically facilitated by continuous and/or repeated detection, by sensor 28, of the factors described hereinabove. In some applications of the invention, feedback is alternatively or additionally provided by subject 22 himself, or by other sensors such as additional feedback sensors (not shown). In addition, other sensors known in the art may be used to obtain feedback and to support feedback control of external device 24 and implant 40. Typically, sensing and responsive modulation of the electrical stimulation parameters is continuous and/or repeated over a duration of time (e.g., more than one hour, e.g., more than 4 hours, e.g., overnight). For severe conditions (e.g., bedridden subjects), sensing and responsive modulation of the electrical stimulation parameters may continue indefinitely.

Reference is made to FIGS. 2A-C, which are schematic illustrations of external device 24, in accordance with some applications of the invention.

Reference is now made to FIG. 2A, which is a schematic illustration of external device 24, in accordance with an application of the invention. External device 24 comprises one or more antennas 30, a control unit 26, and one or more sensors 28. Sensor 28 typically detects one or more parameters of the subject, for example, breathing-related motions, breathing rate, heart rate, heart rhythm, electrical activity (e.g., cardiac electrical activity), blood oxygenation, blood perfusion, sleep pattern and/or other indications of the pathology.

Control unit 26 drives antenna 30 to transmit one or more signals 32, which is received by implant 40 when within an appropriate range. For example, the apparatus may be configured such that implant 40 is typically able to use signals 32 only when the subject is close to external device (e.g., within 10 m, e.g., within 5 m, e.g., within 1 m, e.g., when the subject is in bed). Typically, control unit 26 drives such signal transmission at least in part responsively to the one or more parameters detected by sensor 28. Alternatively or additionally, control unit 26 may drive signal transmission for a pre-determined and/or configurable length of time, or in a particular pattern. For some applications of the invention, signals 32 provide power to implant 40, as described hereinbelow. External device 24 may further comprise one or more additional feedback sensors 44, which detect one or more feedback parameters that indicate the efficacy and/or efficiency of the treatment applied by the implant 40. Alternatively or additionally, the feedback parameters may be the same as the parameters detected by sensor 28, in which case, feedback control is provided without the requirement for feedback sensor 44. Alternatively or additionally, feedback may be provided by the subject himself.

In some applications of the invention, external device 24 may further comprise one or more induction coils 42. Induction coils 42 are configured to supply power, via electromagnetic induction, to implant 40, in conjunction with one or more corresponding induction coils in the implant (not shown). This power may be consumed immediately by implant 40 and/or may be used to charge a power supply, as described hereinbelow.

Reference is now made to FIG. 2B. For some applications of the invention, sensor 28 is external to external device 24. For example, sensor 28 may be coupled to external device 24 by a wire, or may be wirelessly coupled to the external device. Externally-situated sensor 28 allows the sensor to be placed in a position that is suitable for detecting the parameters described hereinabove, whilst external device 24 is disposed in a position that is suitable for transmitting signals 32 to implant 40 and/or supplying wireless power to the implant.

Reference is now made to FIG. 2C. For some applications of the invention, antenna 30 comprises a multidirectional antenna 31 (e.g., a set of mutually-perpendicular antennas), such that signals 32 are receivable by implant 40, independently of the instantaneous orientation of implant 40 in subject 22 (e.g., due to the position of the subject on bed 20). Similarly, implant 40 may comprise a multidirectional antenna for receiving signals 32, generally independently of the orientation of the subject.

Figure 3A:
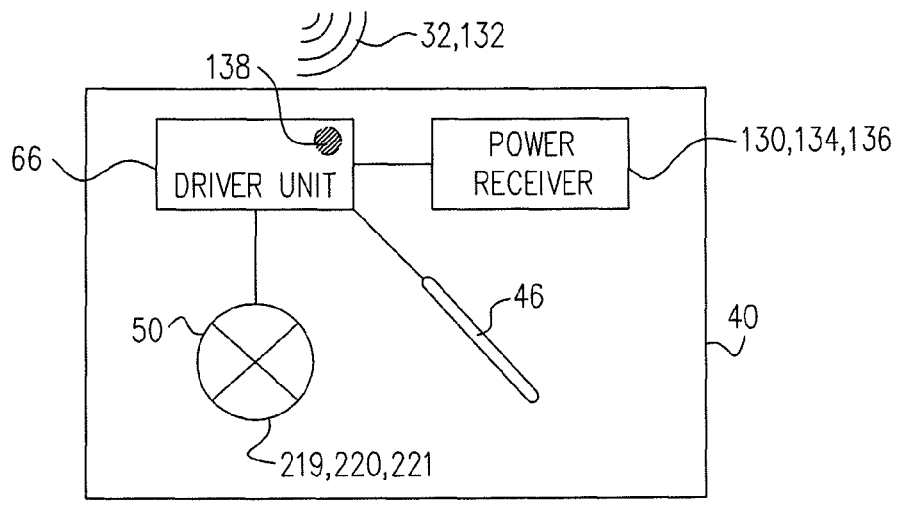
FIGS. 3A-C are schematic illustrations of the implant, comprising electrodes, in accordance with some applications of the present invention.
Figure 3B:
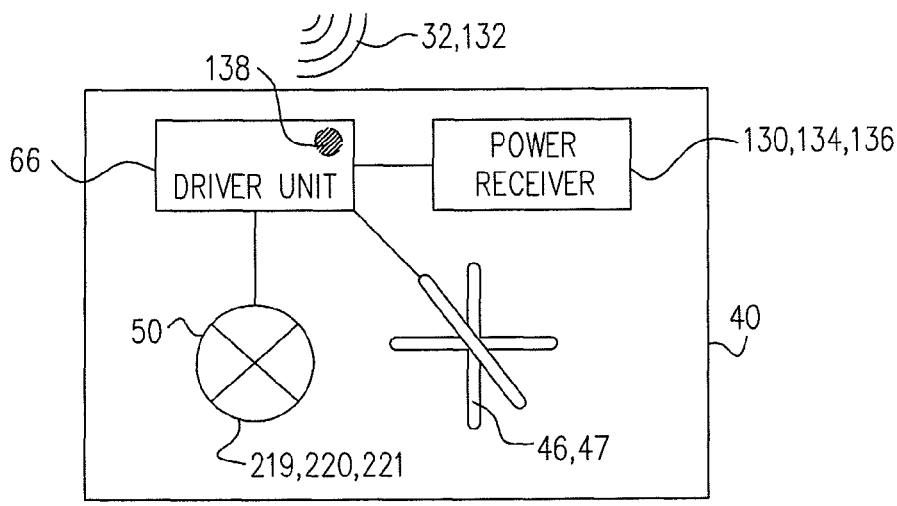
Figure 3C:
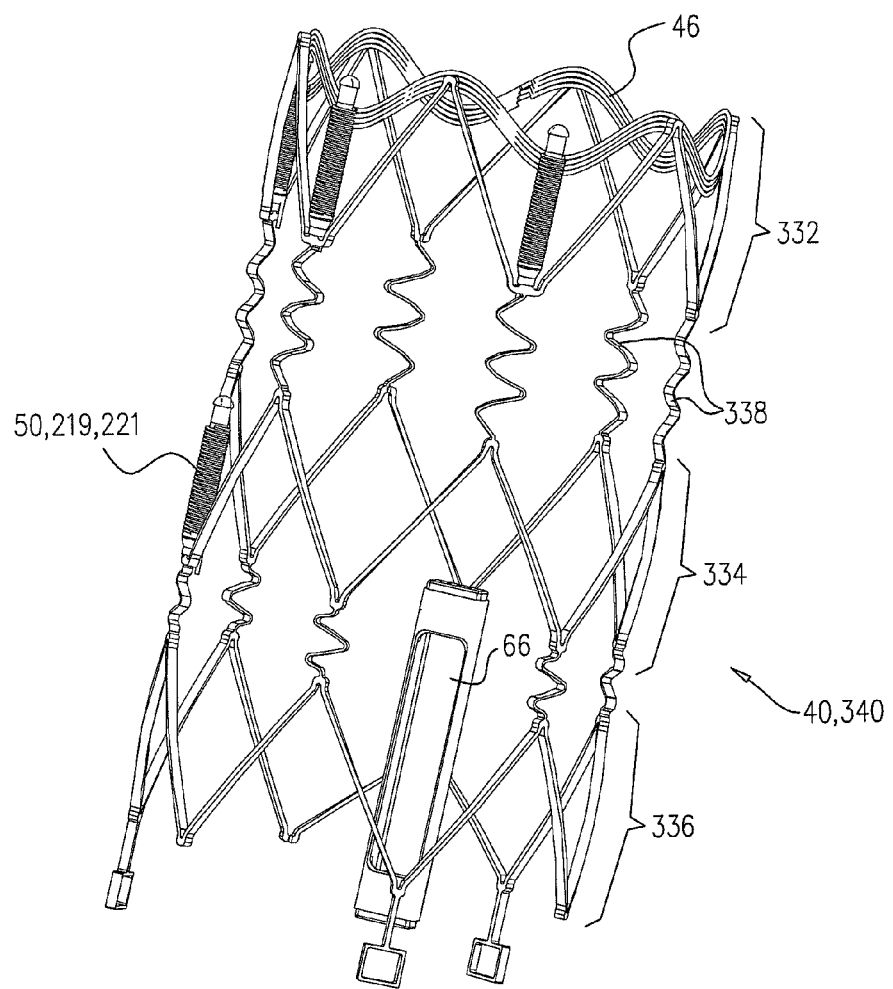

Reference is made to FIGS. 3A-C, which are schematic illustrations of implant 40, in accordance with some applications of the invention.

Reference is now made to FIG. 3A, which is a schematic illustration of implant 40, in accordance with some applications of the invention. Implant 40 typically comprises a driver unit 66, an antenna 46, and an effector element 50. Effector element 50 typically comprises one or more electrodes 219, such as a vagal electrode 220 and/or an aortic electrode 221. In some applications of the invention, effector element 50 also comprises one or more mechanical stimulators, such as piezoelectric actuators, electrical motors, electroactive polymer actuators, and/or balloons, or a combination thereof (not shown). Effector element 50 is typically electronically coupled to driver unit 66. The effector element may be disposed (i.e., implanted) adjacently to driver unit 66, or may be disposed at a different site. Implant 40 typically receives signals 32 from external unit 24, via antenna 46, and drives a current into the implantation site at least in part responsively to the signals, as described hereinbelow. Driver unit 66 typically comprises a power supply 138 (e.g., a battery and/or a capacitor). In some applications of the invention, implant 40 further comprises a power-receiver 130, which receives power wirelessly.

As described with reference to FIGS. 1-2, in some applications of the invention, implant 40 receives power from external unit 24 via electromagnetic induction. In such applications, power-receiver 130 comprises one or more induction coils 134, which typically receive power from induction coils 42 in external device 24.

In some applications of the invention, implant 40 may receive power via electromagnetic radiation (e.g., radio waves and/or microwaves), such as wireless power 132. In such applications of the invention, power-receiver 130 comprises a rectifying antenna (rectenna) 136, which converts wireless power 132 into electrical energy. In some applications of the invention, wireless power 132 may be a dedicated charging signal, transmitted by external device 24. Alternatively or additionally, wireless power 132 may include signals 32, which drive the implant to drive a current into the implantation site such as to at least in part treat the subject's condition. In some applications of the invention, implant 40 either does not comprise antenna 46, or does not comprise power-receiver 30. Rather, signals 32 and wireless power 132 are both received via either antenna 46, or by power-receiver 130.

Electrical energy supplied by power-receiver 130 typically charges power supply 138, such that implant 40 may function in the absence of continuous wireless power. Alternatively or additionally, electrical energy supplied by power-receiver 130 may be consumed by implant 42 as it is supplied. In some applications of the invention, driver unit 66 drives element 50 only while wireless power 132 is being received by power-receiver 130.

Reference is now made to FIG. 3B. For some applications of the invention, antenna 46 comprises a multidirectional antenna 47 (e.g., mutually-perpendicular antennas), such that signals 32 from external device 24 are receivable by implant 40, independently of the orientation of subject 22 (e.g., the position of the subject on bed 20). Similarly, external device 24 may comprise a multidirectional antenna for receiving signals 32, independently of the orientation of the subject.

Reference is now made to FIG. 3C, which is a schematic illustration of implant 40, comprising a stent implant 340, configured to be placed inside a subject's blood vessel, in accordance with some applications of the present invention. At least one electrode 219 (e.g., at least one aortic electrode 221; typically, a plurality of electrodes) is disposed on the stent implant. Typically, stent implant 340 is implanted in the aorta of the subject. However, the scope of the present invention includes placing the stent in any blood vessel of the subject (e.g., the subject's carotid artery, pulmonary artery, and/or renal artery). Typically, stent implant 340 is implanted such that a portion of the stent is disposed in the aortic arch, and a portion of the stent is disposed in the descending aorta. However, the scope of the present invention includes placing the stent at any location within the aorta, such as in the ascending aorta, the descending aorta, the aortic arch, or a combination thereof. For some applications, electrodes 219 are placed in contact with aortic site 224. For example, electrodes 219 may be placed in the area of the aorta that is between (a) the bifurcation of the aorta with a left subclavian artery and (b) the bifurcation of the aorta with a fourth or fifth intercostal artery of the subject.

Typically, the compliance of stent implant 340 varies along the length of the stent. For some applications, the compliance of the stent varies along the length of the stent in a manner that conforms with local stresses exerted on the stent by collagen fibers of the blood vessel. For some applications, the compliance of the stent varies along the length of the stent in a manner that facilitates placement of the stent in a curved blood vessel, the stent being configured to conform with the local shape of the blood vessel.

Typically, stent implant 340 includes a plurality of strut portions along the length of the implant, and the strut portions are coupled to each other at junctions, for example, junctions that include springs 338. Typically, the compliance of implant 340 at the junctions is greater than the compliance of the implant at the strut portions. For some applications, implant 340 is configured to be placed in a curved blood vessel. For some applications, the compliance of the implant at the junctions facilitates curvature of the implant that conforms with the curvature of the blood vessel. For example, the compliance of the implant at the junctions may facilitate curvature of the implant such that local longitudinal axes of respective strut portions of the implant are aligned with local longitudinal axes of a curved blood vessel.

For example, with reference to FIG. 3C, in order to facilitate placement of electrodes 219 at an aortic site as described hereinabove, a first strut portion 332 (e.g., a first row of struts) of implant 340 is placed at the aortic arch, and a second strut portion 334 (e.g., a second row of struts) of the implant is placed in the descending aorta. Alternatively, the second portion is placed in a portion of the aortic arch that is downstream of the aortic arch with respect to the first portion. Upon placement of the first and second portions within the aorta as described, the local longitudinal axis of the first portion of the implant is disposed at an angle from the second portion of the implant. As described hereinabove, in order to facilitate placement of the implant such that the positions of the first and second portions of the implant are as described, the implant defines junctions, e.g., junctions that include springs 338, configured to facilitate bending of the implant, between the first and second portions of the implant. For some applications, the implant defines additional junctions, e.g., additional springs, between other portions of the implant. For example, the implant 340 may define a third strut portion 336 (e.g., a third row of struts) configured to be placed downstream of the second portion. Springs 338 disposed between the second and third portions of the implant facilitate bending of the implant between the second and third portions.

Implant 340 is typically configured to be placed inside the blood vessel (e.g., the aorta) via an endovascular approach, either percutaneously or via a small incision to expose an artery, e.g., using a 12 Fr-20 Fr catheter (e.g., a 14 Fr-18 Fr catheter, such as a 16 Fr catheter). Typically, the arterial access point is through a femoral artery. Typically, upon being placed inside the blood vessel, the implant is partially deployed, such that (a) electrodes 219 contact the wall of the blood vessel at a given location within the blood vessel, and (b) a proximal portion of the implant is disposed inside the catheter, such that the implant may be retrieved into the catheter. The physiological response (e.g., change in heart rate, arterial pressure, and/or ventricular pressure) of the subject to electrical stimulation of the blood vessel at the current location of the electrodes within the blood vessel is determined. In response thereto, the implant is (a) fully deployed at the current location of the implant (b) retrieved into the catheter and redeployed at a different location within the blood vessel, or (c) retrieved into the catheter and removed from the subject's body (e.g., if the subject does not respond in a suitable manner to electrical stimulation of the blood vessel at the locations at which the implant is deployed).

Typically, the compliance of implant 340 is such that pulsation of the blood vessel is substantially maintained upon the implant being deployed inside the blood vessel. Further typically, the implant and components coupled thereto are shaped such as to substantially maintain blood flow through the blood vessel upon deployment of the implant inside the blood vessel.

For some applications, implant 340 is cut from a nitinol tube (or a tube made from a different material, such as stainless steel) having a wall thickness of more than 0.3 mm (e.g., more than 0.4 mm), and/or less than 0.7 mm (e.g., less than 0.6 mm). For some applications the length of the implant is more than 25 mm (e.g., more than 30 mm), and/or less than 50 mm (e.g., less than 40 mm). For some applications, the implant has an outer diameter of more than 10 mm (e.g., more than 15 mm), and/or less than 35 mm (e.g., less than 25 mm). Typically, the implant has a crimped (i.e., compressed) profile of less than 18 Fr (e.g., 12 Fr or less), and/or more than 8 Fr (e.g., 10 Fr or more).

For some applications, one or more portions of implant 340 function as antennas (e.g., antenna 46 and/or antenna 47). For example, the implant may be cut from a nitinol tube and a portion of the tube functions as the antenna. Alternatively, an antenna may be coupled to the implant. For some applications, the diameter of the blood vessel at the antenna is measured using the antenna. For example, impedance between the antenna and the blood vessel wall may be detected, the impedance being indicative of a level of contact between the antenna and the blood vessel wall. The diameter of the blood vessel wall at the antenna is derived from the impedance measurements.

For some applications, implant 340 detects the cardiac cycle of the subject, and provides electrical stimulation at least in part responsively to the cardiac cycle (e.g., only during systole). For some applications, implant 340 is at least partly deformable (e.g., compressible) by the wall of the blood vessel (e.g., the aorta) during the cardiac cycle. For some applications where the implant is thus deformable, and where one or more portions of the implant function as antennas, this deformation of the implant is detectable due to changes in current generated when signals 32 and/or power 132 are received by the antenna. For example, signals 32 and/or power 132 may be transmitted in pulses (e.g., at a frequency of about 5-100 Hz or 100-1000 Hz), and differences in current generated when the pulses are received are interpreted as stages in the cardiac cycle and/or as a heart rate characteristic (e.g., tachycardia, or bradycardia). Typically, but not necessarily, the deformation causes a change in the generated current due to a change in inductance of the antenna.

For some applications, implant 340 provides electrical stimulation at least in part responsively to signals 32 and at least in part responsively to the detected cardiac cycle (e.g., the implant only stimulates during systole). For some applications, external device 24 provides power 132, and implant 340 provides electrical stimulation when the implant receives the power (e.g., when the subject is close to device 24), and at least in part responsively to the detected cardiac cycle.

For some applications, a capsule is coupled to stent implant 340, and driver unit 66 is disposed within the capsule (as shown in FIG. 3C). In some such cases, antenna 46 is disposed within the capsule as well, or coupled to an exterior surface thereof or to the stent.

Reference is again made to FIGS. 3A-C. In some applications, implant 40 may be configured to only respond to signals 32 when the subject is reclining (e.g., when the subject is sleeping). For example, implant 40 may comprise an orientation sensor, such as a gyroscope (e.g., as is known in the cellular telephone art), and driver unit 66 may be configured to drive effector element 50 only when the subject is reclining (e.g., when the subject is sleeping). In some applications (e.g., as described with reference to FIG. 3C), the implant detects the cardiac cycle of the subject, and provides electrical stimulation at the site of implantation at least in part responsively to the cardiac cycle (e.g., only during systole).

The applications of the invention described with reference to FIGS. 1-3 may be combined with those applications described hereinbelow, including those described with reference to FIGS. 4A-5.

Reference is now made to FIGS. 4A-D, which are schematic illustration of electrode implantation sites, in accordance with some applications of the present invention. For some applications of the invention, a subject suffering from the pathology (e.g., CHF, diastolic heart failure, and/or hypertension) is identified. One or more implants 40 are implanted in the vicinity of (e.g., at, or adjacent to) a respective electrode implantation site (i.e., vagal site 222 and/or aortic site 224). One or more electrodes 219 of effector element 50 are implanted at the respective electrode implantation site. For some applications, effector element 50, comprising at least one electrode 219 (e.g., aortic electrode 221) is placed (i.e., implanted) inside the subject's aorta 230 in contact with an aortic site 224. The subject is treated by driver unit 66 electrically stimulating the aortic site, by driving a current into the aortic site, via electrode 219. Typically, driver unit stimulates the aortic site at least in part in response to signals 32 from external unit 24.

Figure 4C:
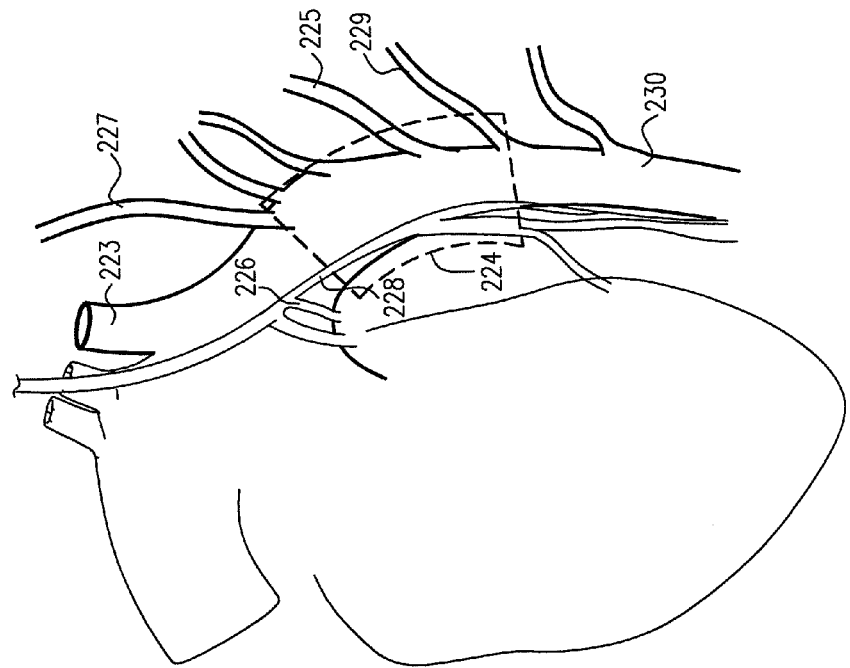
Figure 4D:
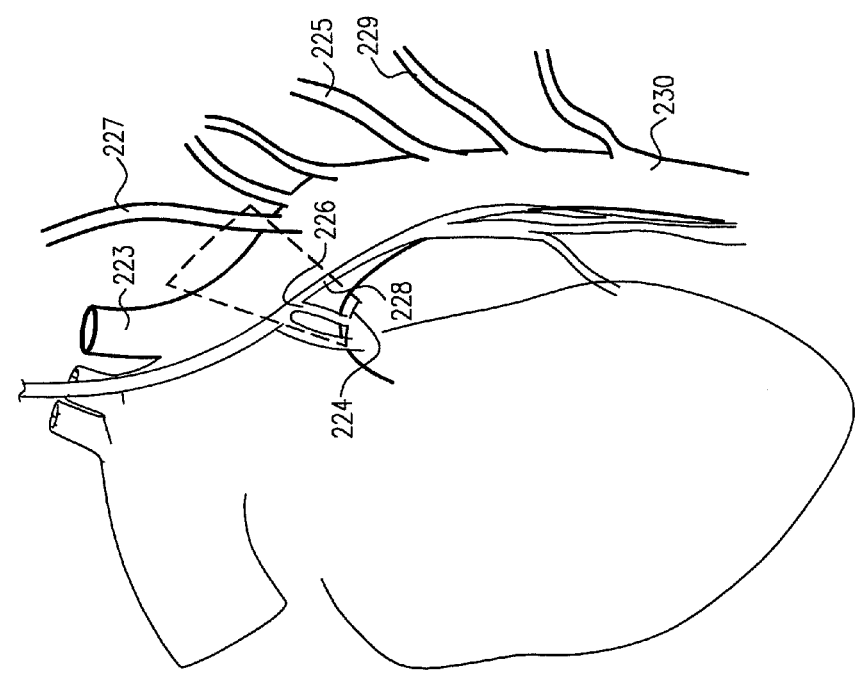

Typically, electrode 219 is placed in contact with an aortic site 224 that is between the bifurcation of aorta 230 with the left subclavian artery 223 and the bifurcation of the aorta with the fifth intercostal artery 229, the aortic site being as shown in FIG. 4A. For example the aortic site may be (a) between the bifurcation of the aorta with the left subclavian artery and a location 4 cm downstream of the bifurcation, (b) between the bifurcation of the aorta with the left subclavian artery and the bifurcation of the aorta with the fourth intercostal artery 225 (the aortic site being as shown in FIG. 4B), (c) between the bifurcation of the aorta with the left subclavian artery and the bifurcation of the aorta with the first intercostal artery 227 (the aortic site being as shown in FIG. 4C), and/or (d) between the bifurcations of the aorta with the first and fifth intercostal arteries (the aortic site being as shown in FIG. 4D). For some applications, the aortic site is adjacent to a portion of a vagus nerve 228 of the subject that is between (a) a vagal bifurcation 226 with a thoracic cardiac branch of the subject (i.e., the thoracic cardiac branch from the left recurrent laryngeal), and (b) thoracic vagal branching into the esophageal plexus of the subject. For some applications, the aortic site is adjacent to a portion of vagus nerve 228 that is slightly proximal to bifurcation 226, e.g., a portion of the vagus nerve between (a) the upper junction of the left thoracic vagal trunk with the left subclavian artery, and (b) bifurcation 226.

Figure 5:
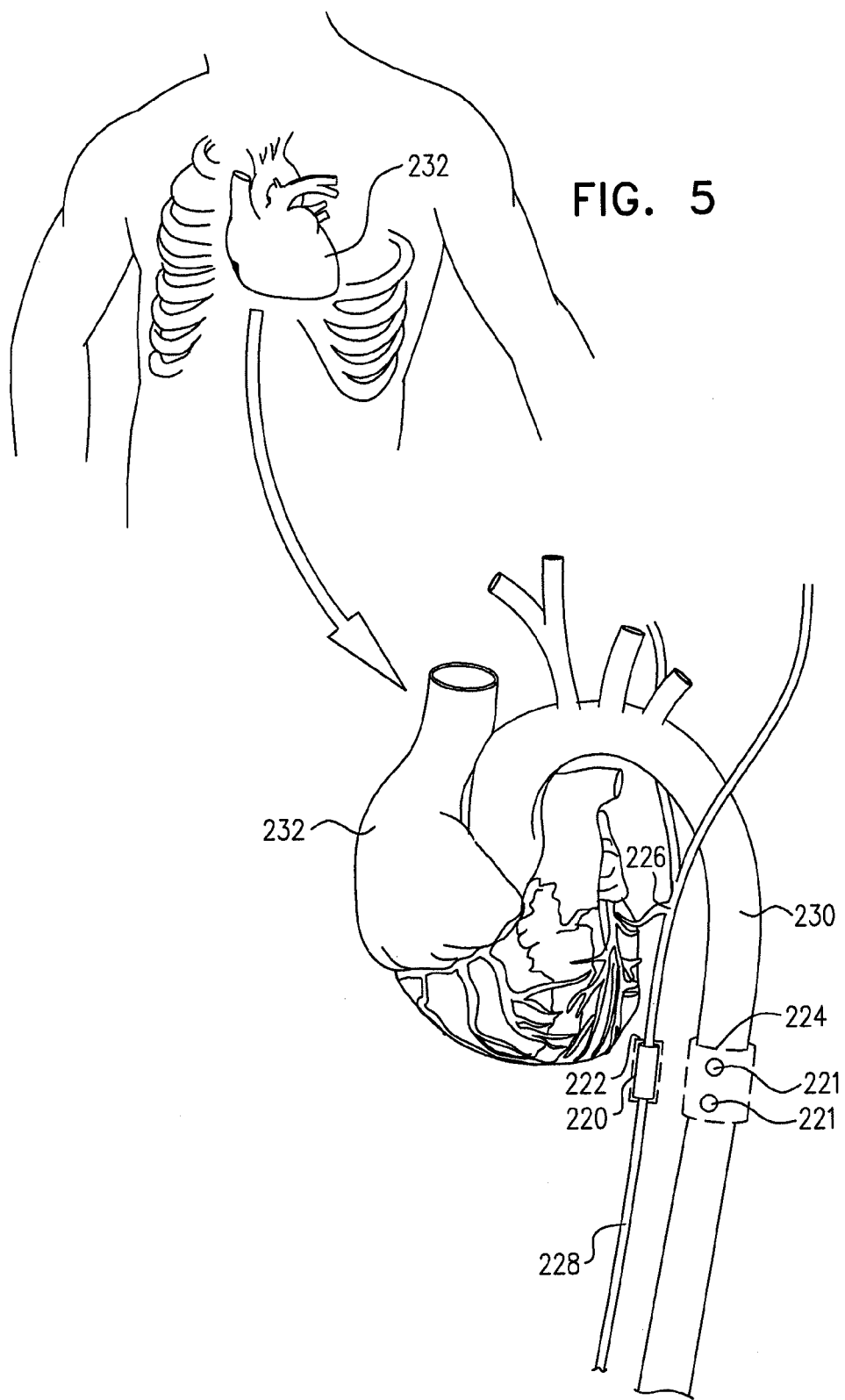
FIG. 5 is a schematic illustration of electrode implantation sites, in accordance with some applications of the invention.

Reference is made to FIG. 5, which is a schematic illustration of vagal site 222 and aortic site 224 of a subject, in accordance with some applications of the present invention. In FIG. 5, vagus nerve 228 is shown separated from aorta 230 for illustrative purposes, although typically the vagus nerve is disposed adjacently to the aorta at an aortic site 224, as shown in FIGS. 4A-D. In general, the anatomy shown in FIG. 5 is not drawn to scale, for illustrative purposes.

For some applications of the invention, one or more implants 40 are implanted in the vicinity of (e.g., at, or adjacent to) a respective element implantation site. Effector element 50, comprising at least one element 219 is placed (i.e., implanted) at vagal site 222. For some applications, vagal site 222 is slightly proximal to bifurcation 226. For example, vagal site 222 may be between (a) the upper junction of the left thoracic vagal trunk with the left subclavian artery, and (b) bifurcation 226. As noted above, the anatomy shown in FIG. 5 is not drawn to scale, for illustrative purposes. It is further noted that the actual location of (a) the vagal bifurcation 226 with the thoracic cardiac branch with respect to (b) aorta 230 is typically as indicated in FIGS. 4A-D, and that FIG. 5 does not show the true relationship between locations of the aorta, the vagus nerve, and the thoracic cardiac branch.

For some applications, aortic electrode 221 is implanted in the vicinity of a portion of the aorta that is adjacent to vagal site 222. For some applications, vagal electrode 220 is implanted on a portion of the vagus nerve that is adjacent to aortic site 224. The subject is treated by driver unit 66 of implant 40 driving a current into one or more of the electrode implantation sites. The effects of driving the current into the implantation site typically include ventricular and aortic pressure reduction, an increase in aortic compliance, a decrease in sympathetic tone, an increase in parasympathetic tone, an increase in ejection fraction, a reduction in heart rate, a reduction in left ventricular wall stress, and/or a reduction in left ventricular myocardial oxygen consumption. For some applications, the electrical stimulation reduces the likelihood of a lethal arrhythmia occurring.

For some applications, an electrode is implanted inside a vein in the vicinity of vagal site 222. For example, the electrode may be implanted in the vena cava, the innominate vein, the subclavian vein, and/or the left or right internal jugular vein. Driver unit 66 drives a current via the intravenously implanted electrode, thereby stimulating the vagal site, in accordance with the techniques described herein. Alternatively or additionally, the electrode is implanted inside an artery of the subject in the vicinity of the vagal site other than (or in addition to) the aorta, such as the pulmonary artery and/or the carotid artery, and a current is driven via the electrode in order to stimulate the vagal site. Alternatively or additionally, the electrode may be implanted at the carotid sinus, and configured to stimulate carotid baroreceptors.

Typically, the current is driven into one or both of the implantation sites, without causing a substantial change in the subject's heart rate. For some applications, there is no substantial effect on the heart rate, because the current is driven into a site that is distal to the thoracic cardiac bifurcation (i.e., the bifurcation of the vagus nerve with the thoracic cardiac branch from the left recurrent laryngeal), and therefore does not have a substantial effect on efferent fibers that directly innervate the subject's heart. (For some applications, stimulating the vagus nerve distally to the thoracic cardiac bifurcation also has a heart rate lowering effect, but it is hypothesized by the inventors that this effect is mediated through central controls rather than direct efferent stimulation of the heart.) Alternatively, the current is driven into an aortic site that is adjacent to a portion of the vagus nerve that is proximal to the thoracic cardiac bifurcation.

For some applications, aortic electrodes 221 are disposed inside the aorta (i.e., electrodes 221 are intravascular electrodes). Alternatively or additionally, the electrodes are disposed in a wall of the aorta. Further alternatively or additionally, vagal electrode 220 is a cuff-electrode (or a different design) that is placed around, or in contact with, the vagus nerve. For some applications, electrode 220 and/or electrodes 221 are chronically implanted at sites 222 and/or 224.

Typically, driver unit 66 of implant 40 drives the current into the electrode implantation site (i.e., vagal site 222 and/or aortic site 224) at least in part in response to signals 32 from external unit 24.

For some applications, driver unit 66 drives the current into the electrode implantation site in coordination with the subject's cardiac cycle and/or respiratory cycle. For example, the subject's ECG may be detected (e.g., by implant 40 and/or by external unit 24), and driver unit 66 may drive the current into the electrode implantation site responsively to the detection of the QRS complex. Alternatively or additionally, the subject's blood pressure may be measured and the current may be driven responsively thereto. For some applications, the subject's ECG, and/or the subject's blood pressure is derived from an electrical signal detected at the aorta, using electrodes 221, or a different set of electrodes (not shown). Alternatively, the current is driven independently of the subject's cardiac cycle and/or respiratory cycle.

For some applications, driver unit 66 driving current into aortic site 224, via electrodes 219, dilates the aorta by increasing nitric oxide (NO) secretion by the wall of the aorta, and/or by increasing the secretion of another vasodilation mediator from the wall of the aorta. Typically, driver unit 66 driving current into aortic site 224, via electrodes 219, inhibits the sympathetic system tone and enhances parasympathetic tone by activation of aortic afferent fibers. For some applications, driver unit 66 driving current into aortic site 224, via electrodes 219, dilates the aorta by stimulating efferent nerve ending. For some applications, driver unit 66 driving current into aortic site 224, via electrodes 219, dilates the aorta by direct electrical hyperpolarization of the vascular smooth muscle.

For some applications, driver unit 66 driving current into vagal site 222 activates afferent aortic signals traveling via the left vagus nerve thereby stimulating autonomic control centers in the central nervous system such as to enhance parasympathetic tone, thereby eliciting a parasympathetic response. For some applications, driver unit 66 driving current into aortic site 224, via electrodes 219, has a similar effect on the vagus nerve (i.e., a vagal response), due to the proximity of aortic site 224 to vagal site 222, and/or due to baroreceptor fibers or nerve endings that are located at the aortic site. For some applications, driver unit 66 driving current into the aortic site generates an aortic response, as described hereinabove, in addition to generating the aforementioned vagal response. For some applications, driver unit 66 driving the current into the aortic site stimulates autonomic control centers in the central nervous system, thereby inhibiting sympathetic tone, and inhibiting sympathetic signaling to the heart and periphery.

For some applications, driver unit 66 driving current into the aortic site, via electrode 219 reduces a ratio of a low frequency component (e.g., less than 0.05 Hz) to a high frequency component (e.g., 0.15-0.35 Hz) of heart rate variability of the subject. For some applications, driver unit 66 driving current into the aortic site, via electrode 219 reduces a ratio of a low frequency component (e.g., less than 0.05 Hz) to a high frequency component (e.g., 0.15-0.35 Hz) of blood pressure variability of the subject.

For some applications, the current has a frequency of more than 5 Hz and/or less than 150 Hz, for example, between 50 Hz and 125 Hz, such as between 100 Hz and 125 Hz. For some applications, the current has an amplitude of between 1 mA and 15 mA, for example, between 3 mA and 12 mA, such as between 7 mA and 10 mA. For some applications, a current having more than two pulses, and/or less than 40 pulses, for example, two pulses to eight pulses, or 30-40 pulses per cardiac cycle, is driven into the aorta. In accordance with respective applications, the current is delivered continuously or intermittently.

For some applications, vagal site 222 is alternatively or additionally mechanically stimulated by implant 40, for example, by mechanically stimulating the vagus nerve at the vagal site, and/or by mechanically stimulating aortic site 224, such that the vagal site also becomes stimulated. For some applications, the vagal site is alternatively or additionally stimulated by implant 40 using the one or more mechanical stimulators described hereinabove (e.g., with reference to FIG. 3A), such as piezoelectric actuators, electrical motors, electroactive polymer actuators, an/or balloons, or a combination thereof.

Reference is again made to FIGS. 4A-5. For some applications, at least one vagal electrode 220 and at least one aortic electrode 221 are implanted, respectively, at a vagal site 222 and an aortic site 224.

The hypothesized effects of the stimulation of vagal site 222 and/or aortic site described with reference to FIGS. 4A-5 are derived from experimental data described in US Patent Applications 2010-0305392 and/or 2011-0137370 to Gross et al., which are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating a subject, the apparatus comprising:
an external device, configured for placement outside of the subject, the external device comprising:
a detector, configured to detect a factor associated with a state of the subject; and
a control unit, couplable to the detector, and configured to automatically generate a signal; and
an implant, comprising:
an antenna, configured to be placed in an artery of the subject and to receive the signal;
an effector element, comprising at least one electrode, and being couplable to an arterial site of the subject; and
a driver unit, coupled to the antenna, and configured to drive the electrode to stimulate an electrode implantation site of the subject, by driving a current into the electrode implantation site, at least in part responsively to the signal,
wherein the control unit is configured to detect a level of impedance of the antenna, and to modulate the signal at least partially in response to the level of impedance of the antenna and the detected factor.

2. The apparatus according to claim 1, wherein the detector is configured to detect the factor associated with the state of the subject, by detecting a factor associated with a disorder of the subject.

3. The apparatus according to claim 1, wherein the detector is configured to detect the factor associated with the state of the subject, by detecting a factor associated with a physiological state of the subject.

4. The apparatus according to claim 1, wherein the driver unit is configured to reduce sympathetic tone of the subject by driving the electrode to stimulate the electrode implantation site of the subject.

5. The apparatus according to claim 1, wherein the driver unit is configured to increase parasympathetic tone of the subject by driving the electrode to stimulate the electrode implantation site of the subject.

6. The apparatus according to claim 1, wherein the detector is configured to detect the factor associated with the state of the subject, by detecting a breathing-related factor of the subject.

7. The apparatus according to claim 1, wherein the detector is configured to detect reclining of the subject, and wherein the control unit is configured to generate the signal at least in part responsively to the reclining of the subject.

8. The apparatus according to claim 1, wherein the detector is configured to detect sitting of the subject, and wherein the control unit is configured to generate the signal at least in part responsively to the detecting of the sitting of the subject.

9. The apparatus according to claim 1, wherein the implant is configured to detect reclining of the subject, and wherein the control unit is configured to drive the effector element at least in part responsively to the reclining of the subject.

10. The apparatus according to claim 1, wherein the detector is configured to detect the factor associated with the state of the subject, by detecting arterial pulses of the subject.

11. The apparatus according to claim 1, wherein the detector is configured to detect the factor associated with the state of the subject, by detecting a body position of the subject.

12. The apparatus according to claim 1, wherein the control unit is configured to generate the signal as a radio frequency signal.

13. The apparatus according to claim 1, wherein the electrode is configured to be placed in contact with an aorta of the subject.

14. The apparatus according to claim 1, wherein the implant is configured to wirelessly receive power.

15. The apparatus according to claim 14, wherein the implant is configured to receive the power from the signal.

16. The apparatus according to claim 14, wherein the implant is configured to receive power via electromagnetic radiation transmitted by the external device.

17. A method for treating a subject, the method comprising:
    extracorporeally detecting a factor associated with a state of the subject;
    automatically, extracorporeally generating a signal;
    intracorporeally receiving the signal at an antenna that is disposed within an artery of the subject;
    detecting a level of impedance at the antenna;
    modulating the signal, at least partially in response to the level of impedance of the antenna and the detected factor, and
    automatically stimulating an electrode implantation site of the subject, by driving a current into the electrode implantation site, at least in part responsively to the signal.

18. The method according to claim 17, wherein extracorporeally detecting the factor comprises extracorporeally detecting a factor associated with a disorder of the subject.

19. The method according to claim 17, wherein extracorporeally detecting the factor comprises extracorporeally detecting a factor associated with a physiological state of the subject.

20. The method according to claim 17, wherein extracorporeally detecting the factor comprises extracorporeally detecting a breathing-related factor of the subject.

21. The method according to claim 17, wherein stimulating the electrode implantation site comprises reducing sympathetic tone of the subject.

22. The method according to claim 17, wherein stimulating the electrode implantation site comprises increasing parasympathetic tone of the subject.

23. The method according to claim 17, wherein intracorporeally receiving the signal comprises wirelessly receiving power via the signal, using an implant that includes the antenna, and wherein automatically stimulating the electrode implantation site comprises powering the implant using the received power.

24. The method according to claim 17,
    wherein intracorporeally receiving the signal comprises wirelessly receiving power via the signal, using an implant that includes the antenna,
    wherein automatically stimulating the electrode implantation site comprises powering the implant using the received power,
    wherein intracorporeally receiving the signal comprises wirelessly receiving data via the signal, using the implant, and
    wherein automatically stimulating the electrode implantation site comprises operating the implant responsively to the received data.

25. The method according to claim 17, wherein generating the signal comprises generating a radio frequency signal, and wherein detecting the signal comprises detecting the radio frequency signal.

26. The method according to claim 17, wherein stimulating the electrode implantation site comprises stimulating an aortic site that is between (a) the bifurcation of the aorta with a left subclavian artery and (b) the bifurcation of the aorta with a fifth intercostal artery of the subject.

27. The apparatus according to claim 1, wherein the control unit is configured to:
    derive from the level of impedance of the antenna, a diameter of the subject's artery; and
    configure the signal in response to the derived diameter of the artery.

28. The method according to claim 17, further comprising deriving from the level of impedance of the antenna, a diameter of the subject's artery, wherein modulating the signal comprising modulating the signal, at least partially responsively to the derived diameter.

29. A method for treating a subject, the method comprising:
    generating a radio frequency signal;
    receiving the radio frequency signal at an antenna that is disposed in a blood vessel of the subject;
    detecting a level of impedance at the antenna;
    electrically stimulating the subject's blood vessel by driving a current into the blood vessel; and
    modulating the current least partially in response to the detected level of impedance.

30. The method according to claim 29, further comprising deriving a diameter of the blood vessel from the detected level of impedance, wherein modulating the current comprises modulating the current at least partially in response to the derived diameter of the blood vessel.

31. The method according to claim 29, wherein the blood vessel includes an aorta of the subject, and wherein electrically stimulating the subject's blood vessel comprises electrically stimulating the subject's aorta.

* * * * *